United States Patent [19]

Hester, Jr.

[11] 4,296,239
[45] Oct. 20, 1981

[54] AMINO-4H-S-TRIAZOLO[4,3-A][1,4]BENZODIAZEPINES

[75] Inventor: Jackson B. Hester, Jr., Galesburg, Mich.

[73] Assignee: The Upjohn Company, Kalamazoo, Mich.

[21] Appl. No.: 61,976

[22] Filed: Jul. 30, 1979

Related U.S. Application Data

[62] Division of Ser. No. 804,627, Jun. 8, 1977, Pat. No. 4,180,668.

[51] Int. Cl.³ .................................... C07D 211/68
[52] U.S. Cl. ............................................ 546/271
[58] Field of Search ................................ 546/271

[56] References Cited

U.S. PATENT DOCUMENTS

| | | | |
|---|---|---|---|
| 4,009,175 | 2/1977 | Hester, Jr. | 546/271 |
| 4,044,129 | 8/1977 | Kuwada et al. | 546/271 |
| 4,180,668 | 12/1979 | Hester, Jr. | 424/267 |

FOREIGN PATENT DOCUMENTS

| | | | |
|---|---|---|---|
| 7340705 | 6/1974 | France | 546/271 |
| 51006994 | 7/1974 | Japan | 546/271 |

OTHER PUBLICATIONS

Hester, Jr., Tetrahedron Letters, No. 20, pp. 1609–1612, (1971).

*Primary Examiner*—Ethel G. Love
*Attorney, Agent, or Firm*—John T. Reynolds

[57] ABSTRACT

6-Amino-4H-s-triazolo[4,3-a][1,4]benzodiazepines of the formula

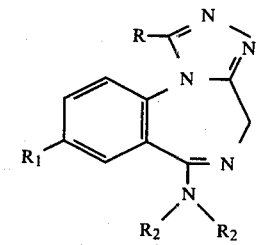

wherein R is hydrogen or $C_1$ to $C_3$-alkyl, $R_1$ is hydrogen or halogen, and the two $R_2$ groups are taken together with the nitrogen to which they are bonded to complete a nitrogen ring moiety selected from the group consisting of pyrrolidino, piperidino, morpholino and 3,6-dihydro-1(2H)-pyridyl, and the pharmacologically acceptable salts thereof, are central nervous system depressant drugs which are useful in effective dosages in domestic and zoo animals for their calming and tranquilizing uses during shipment and to reduce aggressive behavior. In man these compounds are potentially useful for controlling anxiety and schizophrenia and for their sedative, muscle relaxant and anti-convulsant activity.

3 Claims, No Drawings

AMINO-4H-S-TRIAZOLO[4,3-A][1,4]BENZODIAZEPINES

This is a division, of application Ser. No. 804,627, filed June 8, 1977, now U.S. Pat. No. 4,180,668.

INTRODUCTION

This invention relates to triazolo[4,3-a][1,4]benzodiazepine compounds and their use as Central Nervous System (CNS) depressant drugs in mammals, birds and man. More particularly, this invention provides some new 6-amino-4H-s-triazolo[4,3-a][1,4]benzodiazepines which have been found to be useful as CNS depressant drugs useful for a variety of warm blooded animal sedating purposes.

BACKGROUND OF THE INVENTION 1,4-Benzodiazepines having CNS drug tranquilizer utilities have been known since at least 1966. Examples of well known drug products of this type include diazepam and chlordiazepoxide hydrochloride, which are sold under the familiar trademarks VALIUM ® and LIBRIUM ®. Research has continued over the years to find other new and useful 1,4-benzodiazepines which would be competitive with diazepam and chlordiazepoxide hydrochloride, or have different medicinal uses.

Research has prepared compounds varying the 1,4-benzodiazepine structure in the 5-position, putting in different aromatic type heterocyclic rings in the ring C position (5-position). See Archer et al U.S. Pat. No. 3,236,838 and Felix et al U.S. Pat. No. 3,546,212. Also, the Griot U.S. Pat. No. 3,414,563 suggests putting a simple amino group (—NH₂) or an —NRoR₁, or an

—N ring group in the 5-position of the 1,4-benzodiazepine structure. To our knowledge, however, none of these 5-amino 1,4-benzodiazepines have ever become a commercial or useful product to any significant extent.

In my prior U.S. Pat. No. 3,714,178 I have described some 6,7-dihydro-7-alkyl-5H-1,2,4-triazolo[4,3-d][1,4]benzodiazepines of the formula

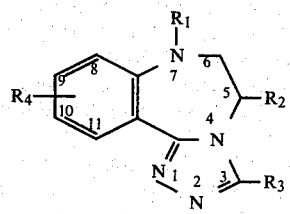

which contain a triazolo ring on the "lower" side of the 1,4-benzodiazepine structure, and U.S. Pat. No. 3,717,654 which describes some 2,5,6,7-tetrahydro-7-alkyl-3H-s-triazolo[4,3-d][1,4]benzodiazepin-3-ones of the formula

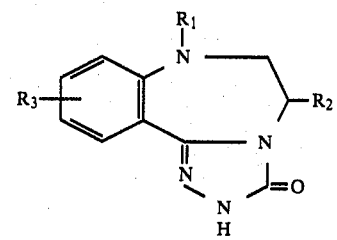

as sedatives, hypnotics, anit-convulsants, tranquilizers and muscle relaxant drugs for mammals and birds and as feed growth additives in livestock and poultry.

My U.S. Pat. No. 3,896,109 describes some 2,3-dihydro-1H-1,4-benzodiazepines of the formula

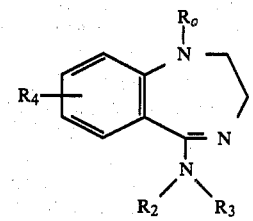

wherein R₂ and R₃ can each be alkyl or R₂ and R₃ taken together with the nitrogen to which they are bonded complete a 4-phenylpiperazino group, which compounds have CNS sedative and tranquilizing properties. This above chemistry is now published in *Tetrahedron Letters*, No. 20, pp. 1609–1612 (1971) in an article entitled "A Synthetic Approach to New 1,4-Benzodiazepine Derivatives", by Jackson B. Hester, Jr., et al.

More recently, Hester U.S. Pat. No. 3,987,052 issued which discloses new 6-phenyl-4H-s-triazolo[4,3-a][1,4]benzodiazepines, e.g., 8-chloro-1-methyl-6-(o-chlorophenyl)-4H-s-triazolo[4,3-a][1,4]benzodiazepines, and the like, which is an important new hypnotic type sedative CNS drug.

However, none of the above 1,4-benzodiazepine prior art patents and references disclose or suggest the new compounds of this invention or what their pharmacological usefulness will be.

OBJECTS OF THE INVENTION

It is an object of this invention to provide some new 6-amino-4H-s-triazolo[4,3-a][1,4]benzodiazepine compounds.

It is a more specific object of this invention to provide a small group of some 6-(N-saturated or mostly saturated heterocyclic)-4H-s-traizolo[4,3-a][1,4]benzodiazepines which are useful in effective dosage forms as CNS depressant drugs useful for calming domestic and zoo animals, and as tranquilizers for tranquilizing animals during shipment and to reduce aggressive behavior.

Other objects, advantages and aspects of the invention will become apparent from reading the remaining specification and the claims which follow.

SUMMARY OF THE INVENTION

Briefly, this invention provides some new 8-halo-6-amino-4H-s-triazolo[4,3-a][1,4]benzodiazepines of the formula

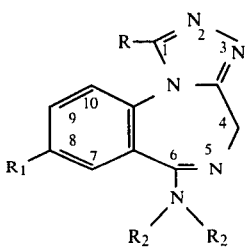

(I)

where R is hydrogen, $C_1$ to $C_3$-alkyl or hydroxymethyl, $R_1$ is hydrogen or a halogen having an atomic number of from 9 to 35, that is, fluorine, chlorine or bromine, and the two $R_2$ moieties are taken together with the nitrogen to which they are bonded to complete a nitrogen ring moiety selected from the group consisting of pyrrolidino, piperidino, morpholino and 3,6-dihydro-1(2H)pyridyl, and the pharmacologically acceptable salts thereof. These compounds have been found to have valuable CNS depressant drug properties in standard laboratory test animals used for that purpose, which properties indicate that these compounds are useful in effective dosage amounts and forms to calm and tranquilize domestic and zoo animals during shipment and to reduce such animals' aggressive behavior. In man, these compounds are potentially useful for controlling anxiety and schizophrenia and for their sedative, muscle relaxing and anti-convulsant activity.

DETAILED DESCRIPTION OF THE INVENTION

Of the above compounds, one of the preferred subgroups of compounds are those wherein R is $C_1$ to $C_3$-alkyl, $R_1$ is halogen having an atomic number of from 9 to 35, and the two $R_2$ groups as taken together with the nitrogen to which they are bonded to complete a piperidino ring group, and the pharmacologically acceptable salts thereof. Examples of such compounds include:
8-fluoro-1-methyl-6-piperidino-4H-s-triazolo[4,3-a][1,4]benzodiazepine,
8-chloro-1-methyl-6-piperidino-4H-s-triazolo[4,3-a][1,4]benzodiazepine,
8-bromo-1-methyl-6-piperidino-4H-s-triazolo[4,3-a][1,4]benzodiazepine,
8-chloro-1-ethyl-6-piperidino-4H-s-triazolo[4,3-a][1,4]benzodiazepine,
8-bromo-1-propyl-6-piperidino-4H-s-triazolo[4,3-a][1,4]benzodiazepine, and the like, and the pharmacologically acceptable salts thereof.

Another preferred subgroup of compounds of formula I are those wherein R is $C_1$ to $C_3$-alkyl, $R_1$ is a halogen having an atomic number of from 9 to 35, and the two $R_2$ groups are taken together with the nitrogen to which they are bonded to complete a 3,6-dihydro-1(2H)-pyridyl, and the pharmacologically acceptable salts thereof. Examples of such compounds include:
8-fluoro-1-ethyl-6-3,6-dihydro-1(2H)-pyridyl)-4H-s-triazolo[4,3-a][1,4]benzodiazepine,
8-chloro-1-methyl-6-3,6-dihydro-1(2H)-pyridyl)-4H-s-triazolo[4,3-a][1,4]benzodiazepines,
8-bromo-1-propyl-6-3,6-dihydro-1(2H)-pyridyl)-4H-s-triazolo[4,3-a][1,4]benzodiazepine, and the like, and their pharmacologically acceptable salts.

Another preferred subgroup of compounds of formula I are those wherein R is $C_1$ to $C_3$-alkyl, $R_1$ is a halogen having an atomic number of from 9 to 35, and the two $R_2$ groups are taken together with the nitrogen to which they are bonded to complete a pyrrolidino ring group, and the pharmacologically acceptable salts thereof. Examples of such compounds include:
8-fluoro-1-methyl-6-pyrrolidino-4H-s-triazolo[4,3-a][1,4]benzodiazepine,
8-chloro-1-ethyl-6-pyrrolidino-4H-s-triazolo[4,3-a][1,4]benzodiazepine,
8-bromo-1-methyl-6-pyrrolidino-4H-s-triazolo[4,3-a][1,4]benzodiazepine, and the like, and their pharmacologically acceptable salts.

Additional compounds of formula 1 of this invention include:
8-fluoro-6-morpholino-4H-s-triazolo[4,3-a][1,4]-benzodiazepine,
8-chloro-6-piperidino-4H-s-triazolo[4,3-a][1,4]-benzodiazepine, 8-bromo-6-pyrrolidino-4H-s-triazolo[4,3-a][1,4]benzodiazepine,
8-chloro-6-3,6-(dihydro-1(2H)-pyridyl)-4H-s-triazolo[4,3-a][1,4]benzodiazepine, and the like, and their pharmacologically acceptable salts thereof.

The acid addition salts of compounds of formula I contemplated in this invention are the hydrochlorides, hydrobromides, hydroiodides, sulfates, phosphates, cyclohexanesulfamates, methanesulfonates, p-toluenesulfonates and the like, prepared by reacting a compound of formula 1 with the stoichiometrically amount of the selected pharmacologically acceptable acid.

The above class of compounds (formula I) has been found to have useful ranges of CNS depressant activities in standard laboratory test animals used to determine those properties. These CNS test results indicate that these compounds are useful in effective dosage quantities and forms for their calming effect, e.g., to tranquilize or alleviate tension and anxiety in domestic or zoo animals such as dogs, cats, monkeys, and the like, during shipment and to reduce aggressive behavior of such animals. These compounds will also be useful for increasing the rate of weight gain in most commercially significant farm animals such as poultry and livestock. In man, these compounds are useful for controlling anxiety and schizophrenia and for their sedative, muscle relaxant and anti-convulsant activity.

The pharmaceutical forms contemplated by this invention include pharmaceutical compositions suited for oral, parenteral and rectal use, e.g., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil, may be used for preparing solutions or suspensions of the active drug. Sweetening, coloring and flavoring agents may be added.

For mammals and birds food premixes, with starch, oatmeal, dried fishmeat, fishmeal, flour and the like can be prepared.

As tranquilizer, the compounds of formula I can be used in dosages of 0.3 mg.–30 mg./kg. in oral or injectable preparations as described above, to alleviate tension and anxiety in mammals, or birds, such as e.g., occurs when animals are in travel. Dosages for use in human subjects as an anti-anxiety agent range from about 3 to about 350 mg. per dose of the active compound of formula I or a pharmaceutically acceptable salt in combination with a pharmaceutically acceptable carrier.

These dosages would be given 1 to 4 times a day depending upon the potency of the particular compound being administered, the condition being treated, the age and weight of the patient, and other factors of concern to the patient's physicians.

For example, it is estimated that the preferred compound, 8-chloro-1-methyl-6-piperidino-4H-s-triazolo[4,3-][1,4]benzodiazepine would be useful as an anti-anxiety drug in humans at dosages which are effective at dosage ranges of 5 to 50 mg. per dosage. Similarly, it is estimated that another preferred compound, 8-chloro-1-methyl-6-3,4-(dihydro-1(2H)-pyridyl)-4H-s-triazolo[4,3-a][1,4]benzodiazepine would be useful as an anti-anxiety drug in humans at dosage ranges of from about 20 to about 200 mg. per dose, depending upon the above-indicated factors. Other compounds of this invention would require dosages of up to about 500 mg. per dose to achieve equivalent CNS effects in humans.

The compounds of this invention can be prepared by a multi-step process starting from 1H-2,4-benzoxazin-1-ones of the formula

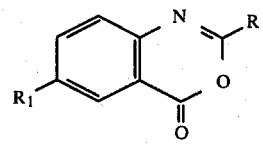

wherein R and $R_1$ are as defined above, which have been described in the literature or can be prepared by the reaction of the appropriately substituted o-aminobenzoic acid with an acid anhydride

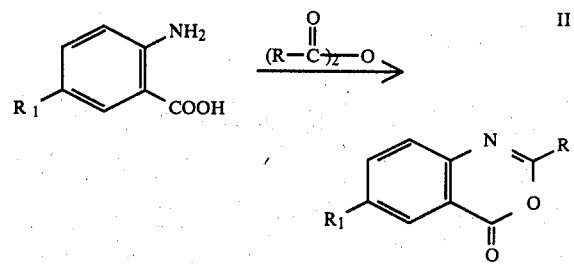

The compounds of this invention can be prepared by at least two different chemical schemes which are illustrated and discussed below.

SCHEME I

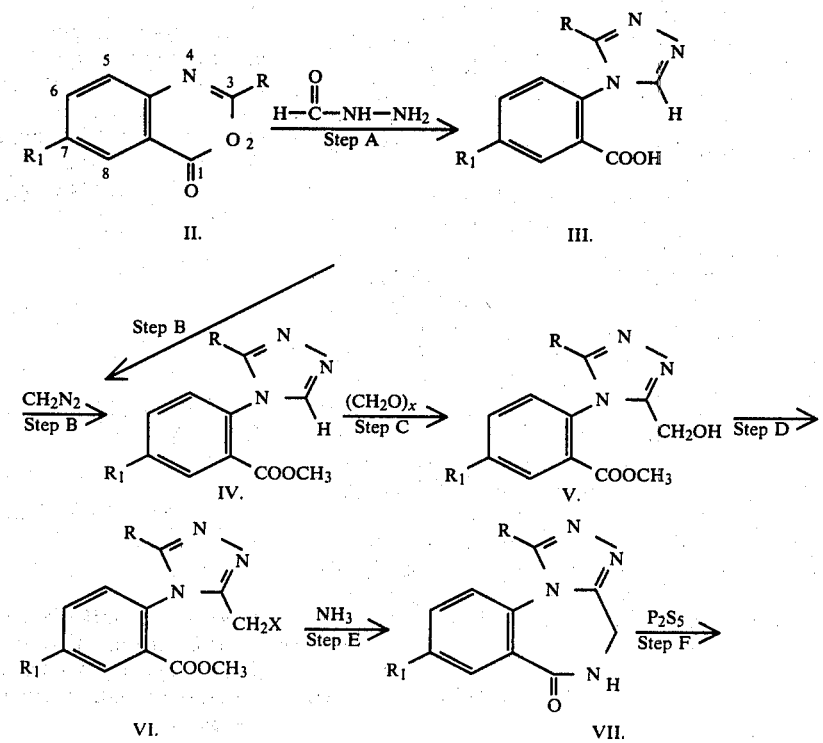

SCHEME I
-continued

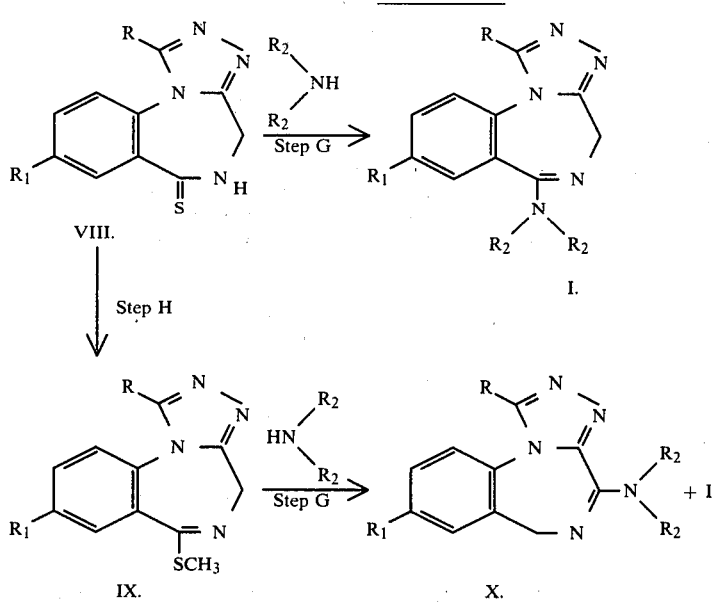

Step A is carried out essentially as described by W. Ried and B. Peters, Ann. Chem. 729, 124 (1969). The appropriately substituted benzooxazinone compound of formula II is allowed to react with formic acid hydrazide in an alkanol solvent (methanol, ethanol, propanol or isopropanol) at the reflux temperature. The reaction requires from 1-5 hours. The benzoic acid product of formula III is isolated by crystallization.

Step B—The benzoic acid (III) from Step A is esterified. Diazomethane in Et$_2$O or CH$_2$Cl$_2$ is convenient but other methods such as the use of oxalyl chloride in benzene to give the acid chloride followed by its reaction with an alkanol will also give the ester in good yield.

Step C—The ester compounds of formula IV are converted to the alcohol compounds of formula V by warming in an inert solvent such as toluene, xylene or chlorobenzene with paraformaldehyde at about 110° to 130° C. The reaction requires from 30 minutes to 5 hours. An excess of paraformaldehyde is usually employed.

Step D—The alcohols of formula V are converted to halides of formula VI by reaction with a variety of halogenating reagents under standard conditions. Thionyl chloride at 50°-70° will give compounds VI (X=Cl) and PBr$_3$ in solvents such as CHCl$_3$, CH$_2$Cl$_2$ at 0°-30° C. will give compounds VI (X=Br).

Step E—The halide compounds of formula VI react with ammonia in solvents such as MeOH, EtOH, THF, etc. to give the 6-oxotriazolobenzodiazepine compounds of formula VII. The reaction may be facilitated, particularly when X=Cl, by an alkali metal iodide. The reaction requires from 9-24 hours at 18°-50° C.

Step F—The 6-oxotriazolobenzodiazepine compounds of formula VII react with phosphorus pentasulfide (P$_2$S$_5$) in solvents such as benzene, toluene, xylene or preferably pyridine at 80°-140° C. to give the 6-thione compounds of formula VIII. When the reaction is carried out in pyridine it requires from 1 to 5 hours at 115°.

Step G—The thione compounds of formula VIII react with amines

to give compounds of formula I. An excess of the amine is usually employed as solvent for the reaction; however, other solvents such as dioxane, n-butanol, etc. can also be used. With the amine as solvent, the reaction is conveniently carried out at the reflux temperature of the amine; however, temperatures of 90°-150° C. are usually operative. The reaction usually requires 18-48 hours.

Step H—The thione compounds of formula VIII can be alkylated with methyl iodide and sodium hydroxide to give the 6-methylthio compounds of formula IX. The reaction is carried out in lower alkanol solvents such as methanol, ethanol or propanol; it requires 30 minutes to 5 hours at 0°-25° C.

Step G'—The 6-methylthio compounds of formula IX react with amines

to give a mixture of compounds I and X. In some cases, e.g., when

represents morpholine, this reaction is greatly facilitated by the addition of a strong tertiary base such as 1,5-diazabicyclo[5.4.0]undec-5-ene (DBU) to the reaction mixture. The reaction is usually run in an excess of the amine

as solvent and requires from 18 to 48 hours at the reflux temperature of the amine (80°–150°). In the absence of amine

DBU in a solvent such as N,N-dimethylsulfoxide (DMSO) will catalyze the conversion of 6-methylthio compound IX to its 4-methylthio- isomer (XIII). This 4-methylthio compound (XIII) will also react with amines

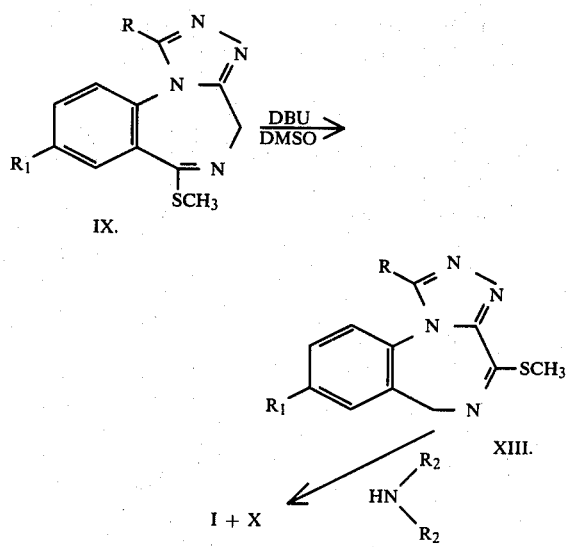

to give compounds of formula I and X.

SCHEME II

The intermediate compounds of formula VIII above, especially those where R=H are also prepared by the following method:

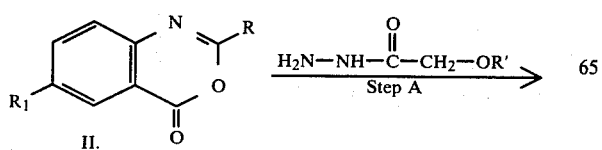

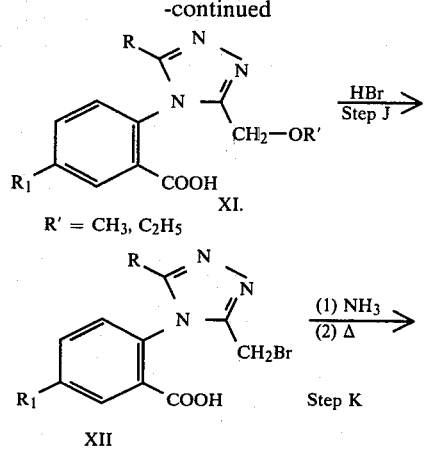

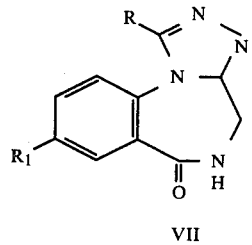

Step A' is carried out in a manner similar to that of Step A by replacing formic acid hydrazide with methoxy or ethoxyacetic acid hydrazide. Better yields are obtained from this reaction if the crude product is allowed to stand with a base such as 20% aqueous sodium carbonate for several hours.

Step J—The methoxy- or ethoxymethyl compounds of formula XI can be converted to the bromide compounds of formula XII by warming with 48% HBr at 80°–100° for 6–24 hours.

Step K—The bromide compounds of formula XII are converted to the 6-oxotriazolobenzodiazepine compounds of formula VII by first allowing them to react with $NH_3$ in solvents such as MeOH, EtOH, THF, dioxane or mixtures thereof for 1–5 hours and then warming the crude product to 200°–250° to complete the cyclization.

Preparation 1:
5-Chloro-2-(3-methyl-4H-1,2,4-triazol-4-yl)benzoic acid

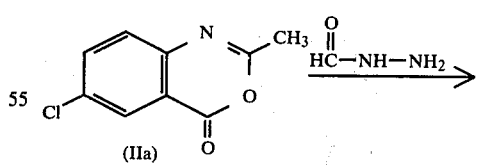

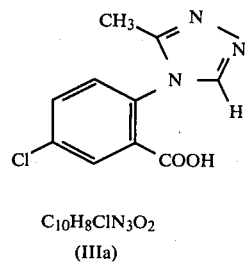

$C_{10}H_8ClN_3O_2$
(IIIa)

A stirred mixture of 7-chloro-3-methyl-1H-2,4-benzoxazin-1-one (IIa)(1.96 g., 0.01 mole), formic acid hydrazide (0.661 g., 0.011 mole) and EtOH (20 ml.) was refluxed, under $N_2$, for 1 hour 50 minutes, cooled and concentrated in vacuo. The residue was crystallized from MeOH to give 1.52 g. of 5-chloro-2-(3-methyl-4H-1,2,4-triazol-4-yl)benzoic acid, melting point 251.5°–253.5° (IIIa). The analytical sample had: melting point 254°–255°; uv (EtOH) end absorption, 224 m$\mu$ (inflection, 11,650), λ max 281 (ϵ 1150), 287 (inflection, 1050). The ir and nmr spectra supported the proposed structure.

Anal. Calcd. for $C_{10}H_8ClN_3O_2$: C, 50.54; H, 3.39; Cl, 14.92; N, 17.68. Found: C, 50.41; H, 3.28; Cl, 14.91; N, 17.66.

In the manner given in Preparation 1 but substituting 1H-2,4-benzoxazine-1-ones with other substituents at C-3 and C-7, the corresponding 5-substituted-2-(3-substituted-4H-1,2,4-triazol-4-yl)benzoic acids can be prepared. Representative compounds thus obtained include:

5-Bromo-2-(3-methyl-4H-1,2,4-triazol-4-yl)benzoic acid,
5-Bromo-2-(3-ethyl-4H-1,2,4-triazol-4-yl)benzoic acid,
5-Bromo-2-(3-n-propyl-4H-1,2,4-triazol-4-yl)benzoic acid,
5-Bromo-2-(4H-1,2,4-triazol-4-yl)benzoic acid,
5-Bromo-2-(3-iso-propyl-4H-1,2,4-triazol-4-yl)benzoic acid,
2-(3-methyl-4H-1,2,4-triazol-4-yl)benzoic acid,
2-(3-ethyl-4H-1,2,4-triazol-4-yl)benzoic acid,
2-(3-propyl-4H-1,2,4-triazol-4-yl)benzoic acid,
2-(3-i-propyl-4H-1,2,4-triazol-4-yl)benzoic acid,
2-(3-iso-propyl-4H-1,2,4-triazol-4-yl)benzoic acid,
2-(4H-1,2,4-triazol-4-yl)benzoic acid,
5-Fluoro-2-(3-methyl-4H-1,2,4-triazol-4-yl)benzoic acid,
5-Fluoro-2-(3-ethyl-4H-1,2,4-triazol-4-yl)benzoic acid,
5-Fluoro-2-(3-iso-propyl-4H-1,2,4-triazol-4-yl)benzoic acid,
5-Fluoro-2-(4H-1,2,4-triazol-4-yl)benzoic acid,
5-Chloro-2-(4H-1,2,4-triazol-4-yl)benzoic acid,
5-Chloro-2-(3-n-propyl-4H-1,2,4-triazol-4-yl)benzoic acid, and the like.

Preparation 2:
5-Chloro-2-(3-methyl-4H-1,2,4-triazol-4-yl)benzoic acid methyl ester

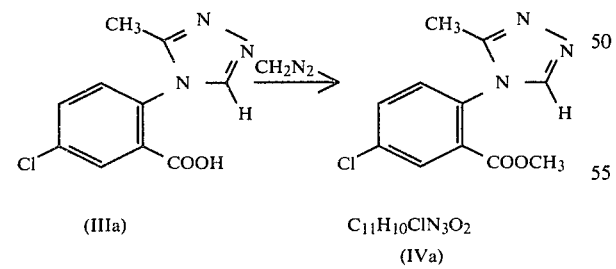

(IIIa)　　　　　$C_{11}H_{10}ClN_3O_2$
　　　　　　　　(IVa)

A stirred suspension of 5-chloro-2-(3-methyl-4H-1,2,4-triazol-4-yl)benzoic acid (IIIa)(77 g.) in methylene chloride (1500 ml.) was cooled in an ice bath and treated with an excess of diazomethane, prepared from 75 g. of N-methyl-N-nitroso-N′-nitroguanidine. The solid quickly dissolved to give a colorless solution. This was washed with dilute $NaHCO_3$ and water, dried ($Na_2SO_4$) and concentrated. The residue was crystallized from benzene-Skellysolve ® B to give 60.8 g. of methyl 5-chloro-2-(3-methyl-4H-1,2,4-triazol-4-yl)benzoate (IVa), melting point 89°–91.5°. The analytical sample had: melting point 86°–88.5°; uv (EtOH) λ max 206 m$\mu$ (ϵ 39,900), 225 (inflection 10,950), 283 (1350), 291 (inflection 1200). The ir and nmr spectra supported the proposed structure.

Anal. Calcd. for $C_{11}H_{10}ClN_3O_2$: C, 52.50; H, 4.01; Cl, 14.09; N, 16.70. Found: C, 52.43; H, 3.98; Cl, 14.04; N, 16.99.

In the manner given in Preparation 2, other 5-substituted-2-(3-substituted-4H-1,2,4-triazol-4-yl)benzoic acid methyl esters can be prepared. Representative compounds thus obtained include:

5-Bromo-2-(3-methyl-4H-1,2,4-triazol-4-yl)benzoic acid methyl ester,
5-Bromo-2-(3-ethyl-4H-1,2,4-triazol-4-yl)benzoic acid methyl ester,
5-Bromo-2-(3-n-propyl-4H-1,2,4-triazol-4-yl)benzoic acid methyl ester,
5-Bromo-2-(4H-1,2,4-triazol-4-yl)benzoic acid methyl ester,
5-Bromo-2-(3-iso-propyl-4H-1,2,4-triazol-4-yl)benzoic acid methyl ester,
2-(3-methyl-4H-1,2,4-triazol-4-yl)benzoic acid methyl ester,
2-(3-ethyl-4H-1,2,4-triazol-4-yl)benzoic acid methyl ester,
2-(3-n-propyl-4H-1,2,4-triazol-4-yl)benzoic acid methyl ester,
2-(3-i-propyl-4H-1,2,4-triazol-4-yl)benzoic acid methyl ester,
5-Fluoro-2-(3-n-propyl-4H-1,2,4-triazol-4-yl)benzoic acid methyl ester,
2-(4H-1,2,4-triazol-4-yl)benzoic acid methyl ester,
5-Fluoro-2-(3-methyl-4H-1,2,4-triazol-4-yl)benzoic acid methyl ester,
5-Fluoro-2-(3-ethyl-4H-1,2,4-triazol-4-yl)benzoic acid methyl ester,
5-Fluoro-2-(3-iso-propyl-4H-1,2,4-triazol-4-yl)benzoic acid methyl ester,
5-Fluoro-2-(4H-1,2,4-triazol-4-yl)benzoic acid methyl ester,
5-Chloro-2-(4H-1,2,4-triazol-4-yl)benzoic acid methyl ester,
5-Chloro-2-(3-n-propyl-4H-1,2,4-triazol-4-yl)benzoic acid methyl ester, and the like.

Preparation 3:
5-Chloro-2-[3-hydroxymethyl)-5-methyl-4H-1,2,4-triazol-4-yl]benzoic acid methyl ester

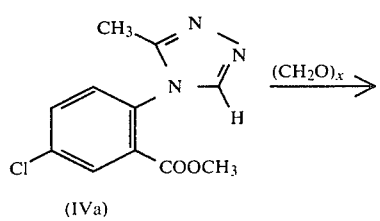

(IVa)

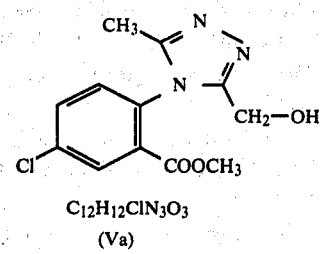

C₁₂H₁₂ClN₃O₃
(Va)

A stirred mixture of methyl 5-chloro-2-(3-methyl-4H-1,2,4-triazol-4-yl)benzoate (IVa)(0.504 g., 0.002 mole, paraformaldehyde (0.6 g.) and xylene (10 ml.) was warmed, under nitrogen, in an oil bath maintained at 115°–124° for one hour 15 minutes and then concentrated in vacuo. The residue was crystallized from an ethanol/ethylacetate mixture to give 0.233 g., melting point 163°–165° and 0.183 g., melting point 157°–159° of 5-chloro-2-[3-(hydroxymethyl)-5-methyl-4H-1,2,4-triazol-4-yl]benzoic acid methyl ester (Va). The analytical sample was recrystallized from MeOH-EtOAc and had: melting point 165°–166.5°; uv (EtOH) λmax 204 mμ (ε 42,600), 225 (inflection, 10,800), 283 (1250). The ir and nmr spectra supported the proposed structure.

Anal. Calcd. for C₁₂H₁₂ClN₃O₃: C, 51.16; H, 4.30; Cl, 12.58; N, 14.92. Found: C, 51.02; H, 4.17; Cl, 12.62; N, 14.67.

In the manner given in preparation 3, other 5-substituted-2-[3-(hydroxymethyl)-5-substituted-4H-1,2,4-triazol-4-yl]benzoic acid methyl esters can be prepared. Representative compounds thus obtained include:

5-Bromo-2-[3-(hydroxymethyl)-5-methyl-4H-1,2,4-triazol-4-yl]benzoic acid methyl ester,
5-Bromo-2-[3-(hydroxymethyl)-5-ethyl-4H-1,2,4-triazol-4-yl]benzoic acid methyl ester,
5-Bromo-2-[3-(hydroxymethyl)-5-n-propyl-4H-1,2,4-triazol-4-yl]benzoic acid methyl ester,
5-Bromo-2-[3-(hydroxymethyl)-4H-1,2,4-triazol-4-yl]benzoic acid methyl ester,
2-[3-(hydroxymethyl)-5-methyl-4H-1,2,4-triazol-4-yl]benzoic acid methyl ester,
2-[3-(hydroxymethyl)-5-ethyl-4H-1,2,4-triazol-4-yl]benzoic acid methyl ester,
2-[3-(hydroxymethyl)-5-n-propyl-4H-1,2,4-triazol-4-yl]benzoic acid methyl ester,
2-[3-(hydroxymethyl)-5-i-propyl-4H-1,2,4-triazol-4-yl]benzoic acid methyl ester,
2-[3,5-bis(hydroxymethyl)-4H-1,2,4-triazol-4-yl]benzoic acid methyl ester,
2-[3-(hydroxymethyl)-4H-1,2,4-triazol-4-yl]benzoic acid methyl ester,
5-Fluoro-2-[3-(hydroxymethyl)-5-methyl-4H-1,2,4-triazol-4-yl]benzoic acid methyl ester,
5-Fluoro-2-[3-(hydroxymethyl)-5-ethyl-4H-1,2,4-triazol-4-yl]benzoic acid methyl ester,
5-Fluoro-2-[3,5-bis(hydroxymethyl)-4H-1,2,4-triazol-4-yl]benzoic acid methyl ester,
5-Fluoro-2-[3-(hydroxymethyl)-4H-1,2,4-triazol-4-yl]benzoic acid methyl ester,
5-Chloro-2-[3-(hydroxymethyl)-4H-1,2,4-triazol-4-yl]benzoic acid methyl ester,
5-Chloro-2-[3-(hydroxymethyl)-5-n-propyl-4H-1,2,4-triazol-4-yl]benzoic acid methyl ester, and the like.

Preparation 4:
5-Chloro-2-[3-(bromomethyl)-5-methyl-4H-1,2,4-triazol-4-yl]benzoic acid methyl ester

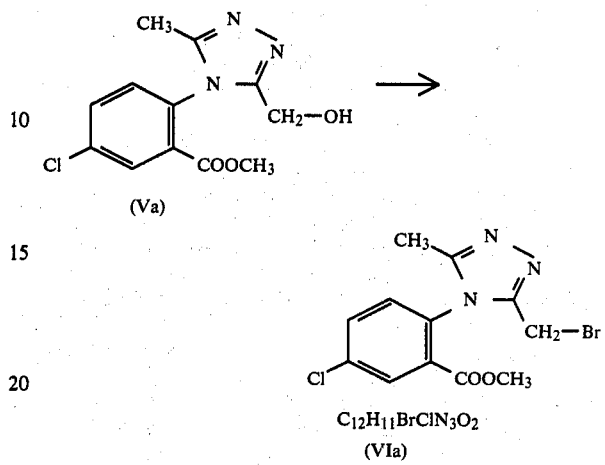

A stirred mixture of 5-chloro-2-[3-(hydroxymethyl)-5-methyl-4H-1,2,4-triazol-4-yl]benzoic acid methyl ester (V) (1.41 g., 0.005 mole) and dry, hydrocarbon-stabilized chloroform (25 ml.) was cooled in an ice bath, under nitrogen, and treated with phosphorus tribromide (0.48 ml.). The initial suspension became a colorless solution during the addition. The mixture was kept in the ice bath for one hour 50 minutes and at ambient temperature for four hours 20 minutes. It was then cooled in an ice bath, treated with methanol (2 ml.), stirred for a few minutes and poured into ice cold, sodium bicarbonate solution. This mixture was extracted with chloroform. The extract was washed with brine, dried (Na₂SO₄) and concentrated in vacuo. The residue was crystallized from a methylene chloride/ethyl acetate mixture to give 0.608 g. of 5-chloro-2-[3-(bromomethyl)-5-methyl-4H-1,2,4-triazol-4-yl]benzoic acid methyl ester (VIa), melting point about 210°–221° dec. This material appeared to be heat sensitive. The analytical sample which was prepared by recrystallizing some of this material from methylene chloride/ethyl acetate at 4° C. had: melting point 210° dec.; uv (EtOH) λ max 206 mμ (ε 46,700), 225 (inflection, 15,800), 281 (1300), 287 (inflection, 1150). The ir and nmr spectra supported the proposed structure.

Anal. Calcd. for C₁₂H₁₁BrClN₃O₂: C, 41.83; H, 3.22; N, 12.19. Found: C, 42.02; H, 3.28; N, 12.54.

In the manner given in preparation 4, other 5-substituted-2-[3-(bromomethyl)-5-substituted-4H-1,2,4-triazol-4-yl]benzoic acid methyl esters can be prepared. Representative compounds thus obtained include:

5-Bromo-2-[3-(bromomethyl)-5-methyl-4H-1,2,4-triazol-4-yl]benzoic acid methyl ester,
5-Bromo-2-[3-(bromomethyl)-5-ethyl-4H-1,2,4-triazol-4-yl]benzoic acid methyl ester,
5-Bromo-2-[3-(bromomethyl)-5-n-propyl-4H-1,2,4-triazol-4-yl]benzoic acid methyl ester,
5-Bromo-2-[3-(bromomethyl)-4H-1,2,4-triazol-4-yl]benzoic acid methyl ester,
5-Bromo-2-[3-(bromomethyl)-5-hydroxymethyl-4H-1,2,4-triazol-4-yl]benzoic acid methyl ester,
2-[3-(bromomethyl)-5-methyl-4H-1,2,4-triazol-4-yl]benzoic acid methyl ester, 2-[3-(bromomethyl)-5-ethyl-4H-1,2,4-triazol-4-yl]benzoic acid methyl ester,
2-[3-(bromomethyl)-5-n-propyl-4H-1,2,4-triazol-4-yl]benzoic acid methyl ester,
2-[3-(bromomethyl)-5-i-propyl-4H-1,2,4-triazol-4-yl]benzoic acid methyl ester,
2-[3-(bromomethyl)-5-(hydroxymethyl)-4H-1,2,4-triazol-4-yl]benzoic acid methyl ester,
2-[3-(bromomethyl)-4H-1,2,4-triazol-4-yl]benzoic acid methyl ester,
5-Fluoro-2-[3-(bromomethyl)-5-methyl-4H-1,2,4-triazol-4-yl]benzoic acid methyl ester,
5-Fluoro-2-[3-(bromomethyl)-5-ethyl-4H-1,2,4-triazol-4-yl]benzoic acid methyl ester,
5-Fluoro-2-[3-(bromomethyl)-5-(hydroxymethyl)-4H-1,2,4-triazol-4-yl]benzoic acid methyl ester,
5-Fluoro-2-[3-(bromomethyl)-4H-1,2,4-triazol-4-yl]benzoic acid methyl ester,
5-Chloro-2-[3-(bromomethyl)-4H-1,2,4-triazol-4-yl]benzoic acid methyl ester,
5-Chloro-2-[3-(bromomethyl)-5-n-propyl-4H-1,2,4-triazol-4-yl]benzoic acid methyl ester, and the like.

Preparation 5:
5-Chloro-2-[3-(chloromethyl)-5-methyl-4H-1,2,4-triazol-4-yl]benzoic acid methyl ester

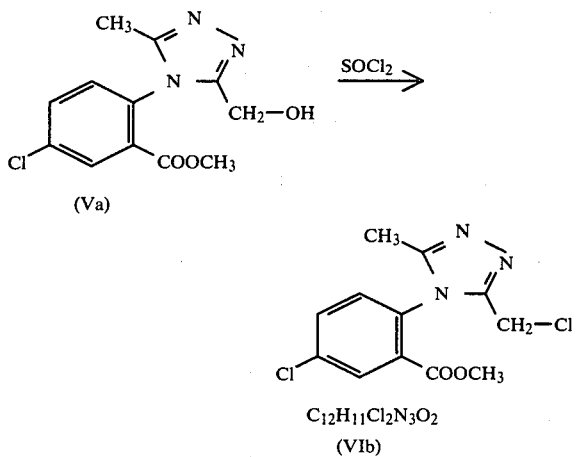

A sample (21.83 g., 0.0776 mole) of 5-chloro-2-[3-(hydroxymethyl)-5-methyl-4H-1,2,4-triazol-4-yl]benzoic acid methyl ester (Va) was added with cooling and stirring to 205 ml. of thionyl chloride. The resulting solution was warmed, under nitrogen, to 55° C. during 65 minutes and maintained at 55°–67° for an additional one hour 35 minutes. It was then concentrated in vacuo. The residue was mixed with dry benzene and concentrated. The resulting material was poured into ice water, neutralized with aqueous sodium bicarbonate solution and extracted with chloroform. The extract was washed with brine, dried (Na2SO4) and concentrated. The solid residue was dissolved in a methylene chloride/ethyl acetate mixture and filtered through a small pad of silica gel. The filtrate was concentrated in vacuo, replacing the methylene chloride by ethyl acetate. The resulting ethyl acetate solution was treated with Skellysolve ® B and allowed to crystallize at 4° C. to give 18.37 g. of 5-chloro-2-[3-(chloromethyl)-5-methyl-4H-1,2,4-triazol-4-yl]benzoic acid methyl ester (VIb), melting point 123°–124°. A second crop, 0.922 g., melting point 120°–120.5°, was obtained by concentrating the mother liquors. The analytical sample was crystallized from EtOAc-Skellysolve ® B and had: melting point 124.5°–126°, uv (EtOH) λ max 206 mµ (ε 47,200), 227 (inflection, 12,350), 281 (1300), 288 (inflection 1150). The ir and nmr spectra supported the proposed structure.

Anal. Calcd. for $C_{12}H_{11}Cl_2N_3O_2$: C, 48.02; H, 3.69; Cl, 23.63; N, 14.00. Found: C, 48.31; H, 3.60; Cl, 23.83; N, 14.21.

In the manner given in preparation 5, other 5-substituted-2-[3-(chloromethyl)-5-substituted-4H-1,2,4-triazol-4-yl]benzoic acid methyl esters can be prepared. Representative compounds thus obtained include:

5-Bromo-2-[3-(chloromethyl)-5-methyl-4H-1,2,4-triazol-4-yl]benzoic acid methyl ester,
5-Bromo-2-[3-(chloromethyl)-5-ethyl-4H-1,2,4-triazol-4-yl]benzoic acid methyl ester,
5-Bromo-2-[3-(chloromethyl)-5-n-propyl-4H-1,2,4-triazol-4-yl]benzoic acid methyl ester,
5-Bromo-2-[3-(chloromethyl)-4H-1,2,4-triazol-4-yl]benzoic acid methyl ester,
5-Bromo-2-[3-(chloromethyl)-5-(hydroxymethyl)-4H-1,2,4-triazol-4-yl]benzoic acid methyl ester,
2-[3-(chloromethyl)-5-methyl-4H-1,2,4-triazol-4-yl]benzoic acid methyl ester,
2-[3-(chloromethyl)-5-ethyl-4H-1,2,4-triazol-4-yl]benzoic acid methyl ester,
2-[3-(chloromethyl)-5-n-propyl-4H-1,2,4-triazol-4-yl]benzoic acid methyl ester,
2-[3-(chloromethyl)-5-i-propyl-4H-1,2,4-triazol-4-yl]benzoic acid methyl ester,
2-[3-(chloromethyl)-5-(hydroxymethyl)-4H-1,2,4-triazol-4-yl]benzoic acid methyl ester,
2-[3-(chloromethyl)-4H-1,2,4-triazol-4-yl]benzoic acid methyl ester,
5-Fluoro-2-[3-(chloromethyl)5-methyl-4H-1,2,4-triazol-4-yl]benzoic acid methyl ester,
5-Fluoro-2-[3-(chloromethyl)-5-ethyl-4H-1,2,4-triazol-4-yl]benzoic acid methyl ester,
5-Fluoro-2-[3-(chloromethyl)-5-(hydroxymethyl)-4H-1,2,4-triazol-4-yl]benzoic acid methyl ester,
5-Fluoro-2-[3-(chloromethyl)-4H-1,2,4-triazol-4-yl]benzoic acid methyl ester,
5-Chloro-2-[3-(chloromethyl)-4H-1,2,4-triazol-4-yl]benzoic acid methyl ester,
5-Chloro-2-[3-(chloromethyl)-5-n-propyl-4H-1,2,4-triazol-4-yl]benzoic acid methyl ester, and the like.

Preparation 6:
8-Chloro-5,6-dihydro-1-methyl-4H-s-triazolo[4,3-a][1,4]benzodiazepin-6-one

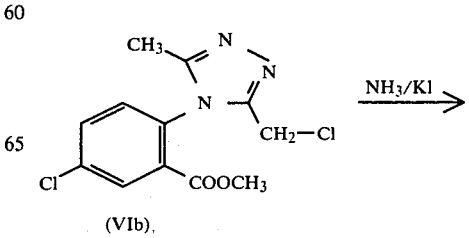

-continued

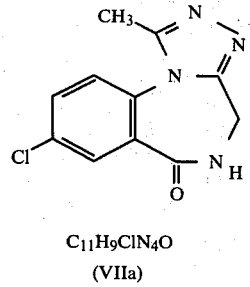

C₁₁H₉ClN₄O
(VIIa)

A stirred solution of 5-chloro-2-[3-(chloromethyl)-5-methyl-4H-1,2,4-triazol-4-yl]benzoic acid methyl ester (VIb)(300 mg., 1 mmole) in tetrahydrofuran (THF) (10 ml.) was cooled, under nitrogen, in an ice bath and treated with 8 ml. of a saturated solution of ammonia in methanol. The mixture was kept in the ice bath for 20 minutes and at ambient temperature for one hour. At this time there was no reaction by thin layer chromatography (TLC). The mixture was therefore treated with potassium iodide (166 mg., 1 mmole) and kept at ambient temperature for 18 hours. It was concentrated in vacuo, and the residue was mixed with water and extracted with chloroform. The extract was washed with brine, dried (Na₂SO₄) and concentrated. The residue was crystallized from a methanol/ethyl acetate mixture to give 0.169 g., melting point 253.5°–255.5° and 0.026 g., melting point 251°–252.5°. The mixture melting point with that of an authentic sample of the titled compound (VIIa) was 261.5°–264.5°. The first crop was recrystallized from a methanol/ethyl acetate mixture, seeding with an authentic sample, to give 0.110 g., melting point 262°–264°. This was identical to the authentic sample of (VIIa) by ir comparison.

In the manner given in preparation 6, other 1,8-substituted-5,6-dihydro-4H-s-triazolo[4,3-a][1,4]benzodiazepin-6-ones can be prepared. Representative compounds thus obtained include:
8-Bromo-5,6-dihydro-1-methyl-4H-s-triazol[4,3-a][1,4]benzodiazepin-6-one,
8-Bromo-5,6-dihydro-1-ethyl-4H-s-triazolo[4,3-a][1,4]benzodiazepin-6-one,
8-Bromo-5,6-dihydro-1-n-propyl-4H-s-triazolo[4,3-a][1,4]benzodiazepin-6-one,
8-Bromo-5,6-dihydro-4H-s-triazolo[4,3-a][1,4]benzodiazepin-6-one,
8-Bromo-5,6-dihydro-1-(hydroxymethyl)-4H-s-triazolo[4-3-a][1,4]benzodiazepin-6-one,
5,6-dihydro-1-methyl-4H-s-triazolo[4,3-a][1,4]benzodiazepin-6-one,
5,6-dihydro-1-ethyl-4H-s-triazolo[4,3-a][1,4]benzodiazepin-6-one,
5,6-dihydro-1-n-propyl-4H-s-triazolo[4,3-a][1,4]benzodiazepin-6-one,
5,6-dihydro-1-i-propyl-4H-s-triazolo[4,3-a][1,4]benzodiazepin-6-one,
5,6-dihydro-1-(hydroxymethyl)-4H-s-triazolo[4,3-a][1,4]benzodiazepin-6-one,
5,6-dihydro-4H-s-triazolo[4,3-a][1,4]benzodiazepin-6-one,
8-Fluoro-5,6-dihydro-1-methyl-4H-s-triazolo[4,3-a][1,4]benzodiazepin-6-one,
8-Fluoro-5,6-dihydro-1-ethyl-4H-s-triazolo[4,3-a][1,4]benzodiazepin-6-one,
8-Fluoro-5,6-dihydro-1-(hydroxymethyl)-4H-s-triazolo[4,3-a][1,4]benzodiazepin-6-one,
8-Fluoro-5,6-dihydro-4H-s-triazolo[4,3-a][1,4]benzodiazepin-6-one,
8-Chloro-5,6-dihydro-4H-s-triazolo[4,3-a][1,4]benzodiazepin-6-one,
8-Chloro-5,6-dihydro-1-n-propyl-4H-s-triazolo[4,3-a][1,4]benzodiazepin-6-one, and the like.

Preparation 7:
5-Chloro-2-[3-(ethoxymethyl)-5-methyl-4H-1,2,4-triazol-4-yl]benzoic acid (XIa)

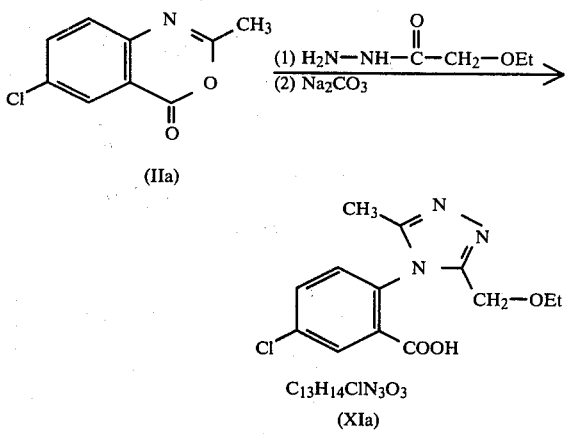

The method of W. Reid and B. Peters, Ann. Chem. 729, 124 (1969) was used for this preparation. A solution of ethoxyacethydrazide (12.4 g., 0.105 mole) in absolute ethanol (105 ml.) was added to a solution of 7-chloro-3-methyl-2,4-benzoxacin-1(2H)-one (IIa) (20.6 g., 0.105 mole) in absolute ethanol (525 ml.); and the resulting mixture was refluxed, under nitrogen, for one hour and 40 minutes, cooled and concentrated in vacuo. The residue was dissolved in 20% aqueous sodium carbonate solution (300 ml.) and stirred at ambient temperature (25° C.) for 18 hours. The resulting mixture was filtered; the filtrate was cooled in an ice bath and acidified (pH 3) with HCl. This mixture was extracted with chloroform. The extract was washed with brine, dried (MgSO₄) and concentrated. The residue crystallized from diethyl ether at 0° C. to give 14.3 g. of the titled compound (XIa), melting point 173°–176°. The analytical sample was recrystallized from methanol/ethyl acetate and had: melting point 175.5°–176.5°; uv (EtOH) end absorption; λ max 224 mμ (inflection 11,400), 281 (ε1100), 288 (inflection 970).

Anal. Calcd. for C₁₃H₁₄ClN₃O₃:
C, 52.80; H, 4.77; Cl, 11.99; N, 14.21. Found: C, 52.74; H, 4.51; Cl, 12.05; N, 14.76.

In the manner given in preparation 7, other 5-substituted-2-[3-(ethoxymethyl)-5-substituted-4H-1,2,4-triazol-4-yl]benzoic acids can be prepared. Representative compounds thus obtained include:
5-Bromo-2-[3-(ethoxymethyl)-5-methyl-4H-1,2,4-triazol-4-yl]benzoic acid,
5-Bromo-2-[3-(ethoxymethyl)-5-ethyl-4H-1,2,4-triazol-4-yl]benzoic acid,
5-Bromo-2-[3-(ethoxymethyl)-5-n-propyl-4H-1,2,4-triazol-4-yl]benzoic acid,
5-Bromo-2-[3-(ethoxymethyl)-4H-1,2,4-triazol-4-yl]benzoic acid, 2-[3-(ethoxymethyl)-5-methyl-4H-1,2,4-triazol-4-yl]benzoic acid,
2-[3-(ethoxymethyl)-5-ethyl-4H-1,2,4-triazol-4-yl]benzoic acid,
2-[3-(ethoxymethyl)-5-n-propyl-4H-1,2,4-triazol-4-yl]benzoic acid,
2-[3-(ethoxymethyl)-5-i-propyl-4H-1,2,4-triazol-4-yl]benzoic acid,
5-fluoro-2-[3-(ethoxymethyl)-5-methyl-4H-1,2,4-triazol-4-yl]benzoic acid,
5-fluoro-2-[3-(ethoxymethyl)-5-ethyl-4H-1,2,4-triazol-4-yl]benzoic acid,
5-fluoro-2-[3-(ethoxymethyl)-4H-1,2,4-triazol-4-yl]benzoic acid,
5-chloro-2-[3-(ethoxymethyl)-4H-1,2,4-triazol-4-yl]benzoic acid,
5-chloro-2-[3-(ethoxymethyl)-5-n-propyl-4H-1,2,4-triazol-4-yl]benzoic acid, and the like.

Preparation 8:
5-Chloro-2-[3-(bromomethyl)-5-methyl-4H-1,2,4-triazol-4-yl]benzoic acid

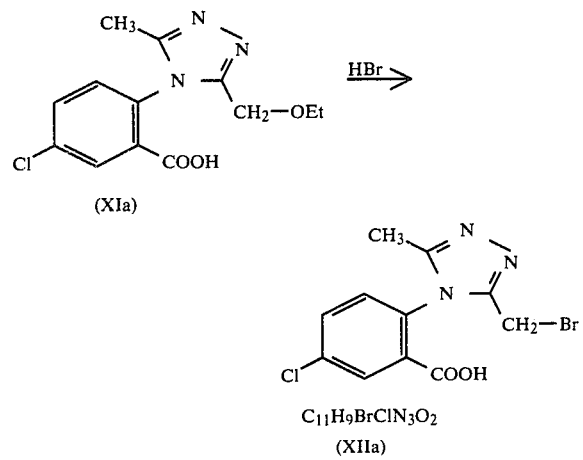

A solution of 5-chloro-2-[3-(ethoxymethyl)-5-methyl-4H-1,2,4-triazol-4-yl]benzoic acid (XIa) (8.86 g., 0.03 mole) in 48% hydrobromic acid (90 ml.) was warmed on the steam bath, under nitrogen for 20 hours and poured into ice water. The pH was adjusted to about 3 with aqueous sodium bicarbonate solution and the resulting solid was collected by filtration, washed with water, dried and recrystallized from a methanol/ethyl acetate mixture to give 2.30 g. of the titled product (XIIa), melting point 243°–245°. The analytical sample had: melting point 248°–250° dec.; uv (EtOH) end absorption, 225 mμ (inflection, 15,750), λ max 281 (ε1150), 289 (inflection, 962). The ir and nmr spectra supported the proposed structure.

Anal. Calcd. for $C_{11}H_9BrClN_3O_2$: C, 39.96; H, 2.74; Br, 24.18; Cl, 10.73; N, 12.71. Found: C, 40.18; H, 2.93; Br, 21.74; Cl, 11.49; N, 12.45.

In the manner given in preparation 8, other 5-substituted-2-[3-(bromomethyl)-5-substituted-4H-1,2,4-triazol-4-yl]benzoic acids can be prepared. Representative compounds thus obtained include:
5-Bromo-2-[3-(bromomethyl)-5-methyl-4H-1,2,4-triazol-4-yl]benzoic acid,
5-Bromo-2-[3-(bromomethyl)-5-ethyl-4H-1,2,4-triazol-4-yl]benzoic acid,
5-Bromo-2-[3-(bromomethyl)-5-n-propyl-4H-1,2,4-triazol-4-yl]benzoic acid,
5-Bromo-2-[3-(bromomethyl)-4H-1,2,4-triazol-4-yl]benzoic acid,
2-[3-(bromomethyl)-5-methyl-4H-1,2,4-triazol-4-yl]benzoic acid,
2-[3-(bromomethyl)-5-ethyl-4H-1,2,4-triazol-4-yl]benzoic acid,
2-[3-(bromomethyl)-5-n-propyl-4H-1,2,4-triazol-4-yl]benzoic acid,
2-[3-(bromomethyl)-5-i-propyl-4H-1,2,4-triazol-4-yl]benzoic acid,
2-[3-(bromomethyl)-4H-1,2,4-triazol-4-yl]benzoic acid,
5-fluoro-2-[3-(bromomethyl)-5-methyl-4H-1,2,4-triazol-4-yl]benzoic acid,
5-fluoro-2-[3-(bromomethyl)-5-ethyl-4H-1,2,4-triazol-4-yl]benzoic acid,
5-fluoro-2-[3-(bromomethyl)-4H-1,2,4-triazol-4-yl]benzoic acid,
5-chloro-2-[3-(bromomethyl)-4H-1,2,4-triazol-4-yl]benzoic acid,
5-chloro-2-[3-(bromomethyl)-5-n-propyl-4H-1,2,4-triazol-4-yl]benzoic acid, and the like.

Preparation 9:
8-Chloro-5,6-dihydro-1-methyl-4H-s-triazolo[4,3-a][1,4]benzodiazepin-6-one

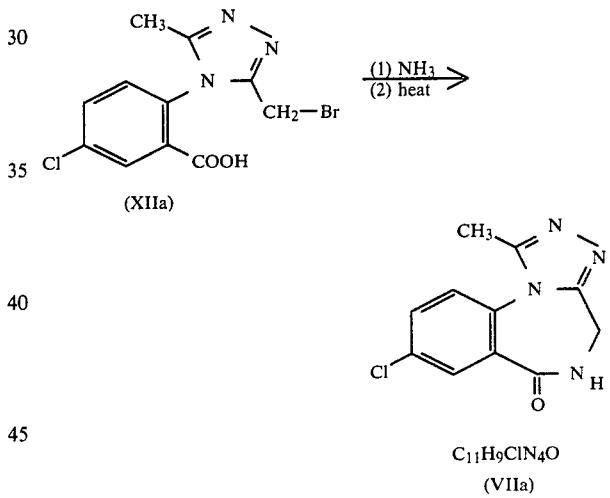

A cold, stirred suspension of 5-chloro-2-[3-(bromomethyl)-5-methyl-4H-1,2,4-triazol-4-yl]benzoic acid (XIIa) (1.95 g., 0.0059 mole) in tetrahydrofuran (THF) (90 ml.) was treated with 74 ml. of methanol that had been saturated with anhydrous ammonia. The mixture was kept at ambient temperature for 2 hours and concentrated in vacuo. The residue was crystallized from methanol/ethyl acetate to give 1.0 g. of solid product, melting point 219°–220.5° dec. This material was warmed under reduced pressure (12 mm.) to 240° in an oil bath. The solid did not melt but changed from a white to a greyish colored solid. The cooled product was crystallized from a methanol/ethyl acetate mixture to give 0.59 g. of 8-chloro-5,6-dihydro-1-methyl-4H-s-triazolo[4,3-a][1,4]benzodiazepin-6-one (VIIa), melting point 263.5°–265°. The analytical sample had: melting point 263°–264°; uv (EtOH) λ max 212 mμ (ε36,450), 236 (17,350), 283 (1500); 291 (inflection, 1350); ir (Nujol) 3320 cm$^{-1}$ (NH), 1655 (C=O). The nmr spectrum supported the proposed structure.

Anal. Calcd. for C₁₁H₉ClN₄O: C, 53.13; H, 3.65; Cl, 14.26; N, 22.53. Found: C, 52.72; H, 3.68; Cl, 14.33; N, 22.68.

In the manner given in preparation 9, other 1,8-substituted-5,6-dihydro-4H-s-triazolo[4,3-a][1,4]benzodiazepin-6-ones can be prepared. Representative compounds thus obtained include:
8-Bromo-5,6-dihydro-1-methyl-4H-s-triazolo[4,3-a][1,4-benzodiazepin-6-one,
8-Bromo-5,6-dihydro-1-ethyl-4H-s-triazolo[4,3-a][1,4benzodiazepin-6-one,
8-Bromo-5,6-dihydro-1-n-propyl-4H-s-triazolo[4,3-a][1,4]benzodiazepin-6-one,
8-Bromo-5,6-dihydro-4H-s-triazolo[4,3-a][1,4]benzodiazepin-6-one,
5,6-dihydro-1-methyl-4H-s-triazolo-[4,3-a][1,4]benzodiazepin-6-one,
5,6-dihydro-1-ethyl-4H-s-triazolo-[4,3-a][1,4]benzodiazepine-6-one,
5,6-dihydro-1-n-propyl-4H-s-triazolo[4,3-a][1,4]benzodiazepin-6-one,
5,6-dihydro-1-i-propyl-4H-s-triazolo[4,3-a][1,4]benzodiazepin-6-one,
5,6-dihydro-4H-s-triazolo[4,3-a][1,4]benzodiazepin-6-one,
8-Fluoro-5,6-dihydro-1-methyl-4H-s-triazolo[4,3-a][1,4]benzodiazepin-6-one,
8-Fluoro-5,6-dihydro-1-ethyl-4H-s-triazolo[4,3-a][1,4]benzodiazepin-6-one,
8-Fluoro-5,6-dihydro-4H-s-triazolo[4,3-a][1,4]benzodiazepin-6-one,
8-Chloro-5,6-dihydro-4H-s-triazolo[4,3-a][1,4]benzodiazepin-6-one,
8-Chloro-5,6-dihydro-1-n-propyl-4H-s-triazolo[4,3-a][1,4]benzodiazepin-6-one, and the like.

Preparation 10:
8-Chloro-4,5-dihydro-1-methyl-6H-s-triazolo[4,3-a][1,4]benzodiazepine-6-thione

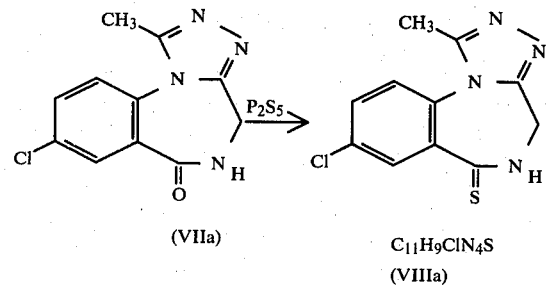

(VIIa)

C₁₁H₉ClN₄S
(VIIIa)

A stirred mixture of 8-chloro-5,6-dihydro-1-methyl-4H-s-triazolo[4,3-a][1,4]benzodiazepin-6-one (VIIa) (24.87 g., 0.1 mole) and dry pyridine (1420 ml.) was treated with phosphorus pentasulfide (24.45 g., 0.11 mole) and refluxed for 2.5 hours, under nitrogen. The mixture was cooled, concentrated in vacuo, and the residue mixed with water and chloroform. The mixture was neutralized with sodium bicarbonate and the solid collected by filtration. This solid was washed with chloroform and recrystallized from a chloroform/methanol/ethyl acetate mixture to give 20.31 g., melting point 303°-308° of the titled product (VIIIa). Additional product was obtained from the chloroform filtrates which were washed with brine, dried (Na₂SO₄) and concentrated. The residue was crystallized from a chloroform/methanol/ethyl acetate mixture to give 2.93 g., melting point 298°-303°; and 0.78 g., melting point 302°-305° of the title compound (VIIIa) (91% overall yield). The analytical sample was recrystallized from methylene chloride/methanol and had: melting point 306°-308°; uv (EtOH) λ max 223 mμ (ε31,500), 316 (7700). The ir and nmr spectra support the proposed structure.

Anal. Calcd. for C₁₁H₉ClN₄S: C, 49.91; H, 3.43; Cl, 13.39; N, 21.16; S, 12.11. Found: C, 50.20; H, 3.48; Cl, 13.51; N, 21.39; S, 12.29.

In the manner given in preparation 10, other 1,8-substituted-4,5-dihydro-6H-s-triazolo[4,3-a][1,4]benzodiazepine-6-thiones can be prepared. Representative compounds thus obtained include:
8-Bromo-4,5-dihydro-1-methyl-6H-s-triazolo[4,3-a][1,4]benzodiazepine-6-thione,
8-Bromo-4,5-dihydro-1-ethyl-6H-s-triazolo[4,3-a][1,4]benzodiazepine-6-thione,
8-Bromo-4,5-dihydro-1-n-propyl-6H-s-triazolo[4,3-a][1,4]benzodiazepine-6-thione,
8-Bromo-4,5-dihydro-6H-s-triazolo[4,3-a][1,4]benzodiazepine-6-thione,
8-bromo-4,5-dihydro-1-(hydroxymethyl)-6H-s-triazolo[4,3a][1,4]-benzodiazepine-6-thione,
4,5-dihydro-1-methyl-6H-6H-s-triazolo[4,3-a][1,4]benzodiazepine-6-thione,
4,5-dihydro-1-ethyl-6H-s-triazolo[4,3-a][1,4]benzodiazepine-6-thione,
4,5-dihydro-1-n-propyl-6H-s-triazolo[4,3-a][1,4]benzodiazepine-6-thione,
4,5-dihydro-1-i-propyl-6H-s-triazolo[4,3-a][1,4]benzodiazepine-6-thione,
4,5-dihydro-1-(hydroxymethyl)-6H-s-triazolo[4,3-a][1,4]benzodiazepine-6-thione,
5,6-dihydro-4H-s-triazolo[4,3-][1,4]benzodiazepine-6-thione,
8-Fluoro-4,5-dihydro-1-methyl-6H-s-triazolo[4,3-a][1,4]benzodiazepine-6-thione,
8-Fluoro-4,5-dihydro-1-ethyl-6H-s-triazolo[4,3-a][1,4]benzodiazepine-6-thione,
8-Fluoro-4,5-dihydro-1-(hydroxymethyl)-6H-s-triazolo[4,3-a][1,4]benzodiazepine-6-thione,
8-Fluoro-4,5-dihydro-6H-s-triazolo[4,3-a][1,4]benzodiazepine-6-thione,
8-Chloro-4,5-dihydro-6H-s-triazolo[4,3-a][1,4]benzodiazepine-6-thione,
8-Chloro-4,5-dihydro-1-n-propyl-6H-s-triazolo[4,3-a][1,4]benzodiazepine-6-thione, and the like.

Preparation 11:
8-Chloro-1-methyl-6-(methylthio)-4H-s-triazol[4,3-a][1,4]benzodiazepine

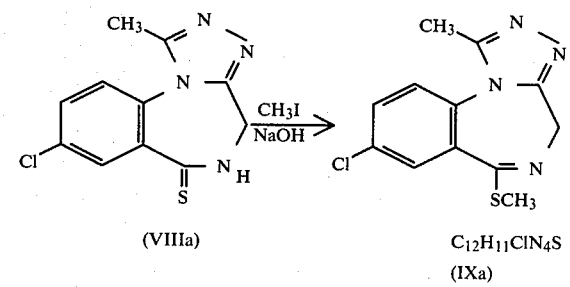

(VIIIa)

C₁₂H₁₁ClN₄S
(IXa)

An ice cold, stirred mixture of 8-chloro-4,5-dihydro-1-methyl-6H-s-triazolo[4,3-a][1,4]benzodiazepine-6-thione (VIIIa) (13.2 g., 0.05 mole) in methanol (75 ml.)

was treated with 55 ml. of 0.945 N aqueous sodium hydroxide solution. The ice bath was removed and after 10 minutes methyl iodide (3.11 ml., 0.05 mole) was added to the solution. About 5 minutes after this addition the mixture solidified. It was kept at ambient temperature for one hour, mixed with ice water and stirred for 10 minutes. The solid was collected by filtration, washed with water and dried to give 12.0 g. of the title compound, IXa, melting point 244°–249°. The analytical sample was recrystallized from methylene chloride-/ethyl acetate and had melting point 247.5°–249°.

Anal. Calcd. for $C_{12}H_{11}ClN_4S$: C, 51.70; H, 3.98; Cl, 12.72; N, 20.10; S, 11.50. Found: C, 51.71; H, 4.19; Cl, 12.92; N, 19.87; S, 11.59.

In the manner given in preparation 11, other 1,8-disubstituted-6-(methylthio)-4H-s-triazolo[4,3-a][1,4]benzodiazepines can be prepared. Representative compounds thus obtained include:
8-Bromo-1-methyl-6-(methylthio)-4H-s-triazolo[4,3-a][1,4]benzodiazepine,
8-Bromo-1-ethyl-6-(methylthio)-4H-s-triazolo[4,3-a][1,4]benzodiazepine,
8-Bromo-1-n-propyl-6-(methylthio)-4H-s-triazolo[4,3-a][1,4]benzodiazepine,
8-Bromo-6-(methylthio)-4H-s-triazolo[4,3-a][1,4]benzodiazepine,
8-Bromo-1-(hydroxymethyl)-6-(methylthio)-4H-s-triazolo[4,3-a][1,4]benzodiazepine,
1-Methyl-6-(methylthio)-4H-s-triazolo[4,3-a][1,4]benzodiazepine,
1-Ethyl-6-(methylthio)-4H-s-triazolo[4,3-a][1,4]benzodiazepine,
1-n-propyl-6-(methylthio)-4H-s-triazolo[4,3-a][1,4]benzodiazepine,
1-i-propyl-6-(methylthio)-4H-s-triazolo[4,3-a][1,4]benzodiazepine,
1-hydroxymethyl)-6-(methylthio)-4H-s-triazolo[4,3-a][1,4]benzodiazepine,
6-methylthio-4H-s-triazolo[4,3-a][1,4]benzodiazepine,
8-Fluoro-1-methyl-6-(methylthio)-4H-s-triazolo[4,3-a][1,4]benzodiazepine,
8-Fluoro-1-ethyl-6-(methylthio)-4H-s-triazolo[4,3-a][1,4]benzodiazepine,
8-Fluoro-1-(hydroxymethyl)-6-(methylthio)-4H-s-triazolo[4,3-a][1,4]benzodiazepine,
8-Fluoro-6-(methylthio)-4H-s-triazolo[4,3-a][1,4]benzodiazepine,
8-Chloro-6-(methylthio)-4H-s-triazolo[4,3-a][1,4]benzodiazepine,
8-Chloro-1-n-propyl-6-(methylthio)-4H-s-triazolo[4,3-a][1,4]benzodiazepine, and the like.

Preparation 12:
8-Chloro-1-methyl-4-(methylthio)-6H-s-triazolo[4,3-a][1,4]benzodiazepine (XIIIa)

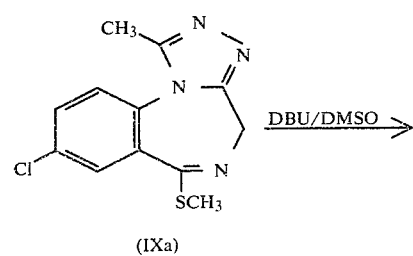

(IXa)

-continued

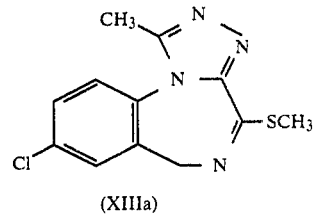

(XIIIa)

A stirred mixture of 8-chloro-1-methyl-6-(methylthio)-4H-s-triazolo[4,3-a][1,4]benzodiazepine, (1.118 g., 0.004 mole) in dry N,N-dimethylsulfoxide (9 ml.) was treated with 0.608 g. (0.004 mole) of 1,5-diazabicyclo[5.4.0]undec-5-ene (DBU). The resulting mixture was kept at ambient temperature for 1 hour and 15 minutes, warmed slowly to 100° C. during about 2 hours and kept at 100° C. for 3 hours and 45 minutes. The resulting mixture was poured onto crushed ice and extracted with chloroform. The extract was washed with water, dried over sodium sulfate and concentrated. The residue was chromatographed on silica gel (75 g.) with 2% methanol in chloroform. The first compound eluted was crystallized from a methylene chloride-/ethyl acetate mixture to give 0.203 g. of a crop having a melting point of 148.5°–250° C. and a 0.051 g. crop having a melting point of 248.5° to 250° c. of 8-chloro-1-methyl-4-(methylthio)-6H-s-triazolo[4,3-a][1,4]benzodiazepine. The analytical sample had a melting point of 249.5°–250.5° C.

Anal. Calcd. for $C_{12}H_{11}ClN_4S$: C, 51.70; H, 3.98; Cl, 12.72; N, 20.10; S, 11.50. Found: C, 51.79; H, 3.92; Cl, 12.25; N, 20.03; S, 11.61.

The second compound eluted from the column was crystallized from a methylene chloride/ethyl acetate mixture to give 0.369 g. of a crop melting at 248.5°–251° C., and a crop weighing 0.141 g. melting at 248.5° to 250° C. of recovered 6-methylthio starting material (IXa).

EXAMPLE 1

8-Chloro-1-methyl-6-piperidino-4H-s-triazolo[4,3-a][1,4]benzodiazepine (Ia)

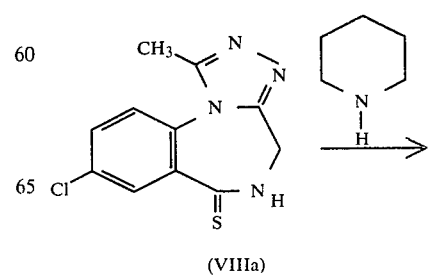

(VIIIa)

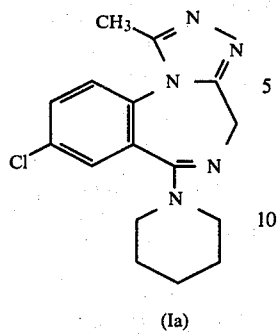

(Ia)

A stirred solution of 8-chloro-4,5-dihydro-1-methyl-6H-s-triazolo[4,3-a][1,4]benzodiazepine-6-thione (VIIIa) (2.65 g., 0.01 mole) and piperidine (25 ml.) was refluxed for 18 hours, under nitrogen. The solution was mixed with cold water and extracted with methylene chloride. The extract was washed with water, then brine, dried ($Na_2SO_4$) and concentrated in vacuo. The solid residue was mixed with ethyl acetate and collected by filtration; it was recrystallized from a methylene chloride/methanol/ethyl acetate mixture to give 1.39 g., melting point 238°–243° (soften 235) and 0.40 g., melting point 225°–232° (soften 220) of the titled compound (Ia) (57% yield). The analytical sample had: melting point 248°–249.5° (soften 235°), uv (EtOH) λ max 214 mμ (ε34,850), 235 (sh, 13,200), 287 (sh, 2950), 293 (3050). The ir and nmr spectra support the proposed structure.

Anal. Calcd. for $C_{16}H_{18}ClN_5$: C, 60.85; H, 5.74; Cl, 11.23; N, 22.18. Found: C, 60.60; H, 5.74; Cl, 11.33; N, 22.24.

In the manner given in Example 1, other 1,8-disubstituted-6-piperidino-4H-s-triazolo[4,3-a][1,4 benzodiazepines can be prepared. Representative compounds thus obtained include:

8-Bromo-1-methyl-6-piperidino-4H-s-triazolo[4,3-a][1,4]benzodiazepine,
8-Bromo-1-ethyl-6-piperidino-4H-s-triazolo[4,3-a][1,4]benzodiazepine,
8-Bromo-1-n-propyl-6-piperidino-4H-s-triazolo[4,3-a][1,4]benzodiazepine,
8-Bromo-6-piperidino-4H-s-triazolo[4,3-a][1,4]benzodiazepine,
8-Bromo-1-(hydroxymethyl)-6-piperidino-4H-s-triazolo-[4,3-a][1,4]benzodiazepine,
1-Methyl-6-piperidino-4H-s-triazolo[4,3-a][1,4]benzodiazepine,
1-Ethyl-6-piperidino-4H-s-triazolo[4,3-a][1,4]benzodiazepine,
1-n-propyl-6-piperidino-4H-s-triazolo[4,3-a][1,4]benzodiazepine,
1-i-propyl-6-piperidino-4H-s-triazolo[4,3-a][1,4]benzodiazepine,
1-(hydroxymethyl)-6-piperidino-4H-s-triazolo[4,3-a][1,4]benzodiazepine,
6-piperidino-4H-s-triazolo[4,3-a][1,4]benzodiazepine,
8-Fluoro-1-methyl-6-piperidino-4H-s-triazolo[4,3-a][1,4]benzodiazepine,
8-Fluoro-1-ethyl-6-piperidino-4H-s-triazolo[4,3-a][1,4]benzodiazepine,
8-Fluoro-1-(hydroxymethyl)-6-piperidino-4H-s-triazolo[4,3][1,4]benzodiazepine,
8-Fluoro-6-piperidino-4H-s-triazolo[4,3-a][1,4]-benzodiazepine,
8-Chloro-6-piperidino-4H-s-triazolo[4,3-a][1,4]benzodiazepine,
8-Chloro-1-n-propyl-6-piperidino-4H-s-triazolo-[4,3-a][1,4]benzodiazepine and the like.

EXAMPLE 2

8-Chloro-6-(3,6-dihydro-1(2H)-pyridyl)-1-methyl-4H-s-triazolo-[4,3-a][1,4]benzodiazepine (Ib)

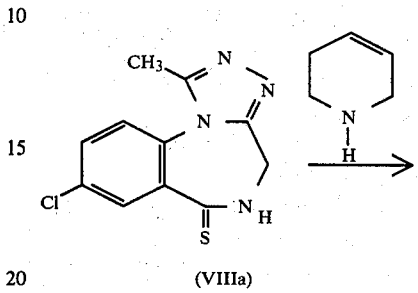

(VIIIa)

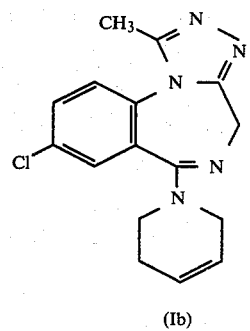

(Ib)

A stirred mixture of 8-Chloro-4,5-dihydro-1-methyl-6H-s-triazolo[4,3-a][1,4]benzodiazepine-6-thione (2.65 g., 0.01 mole) and 1,2,3,6-tetrahydropyridine (15 ml.) was refluxed for 32 hours with a slow stream of nitrogen passing through the mixture. It was then kept at ambient temperature for three days, mixed with water and extracted with methylene chloride; the aqueous layer was saturated with sodium chloride and re-extracted with methylene chloride. The combined extracts were washed with brine, dried ($Na_2SO_4$) and concentrated. The residue was crystallized from methylene chloride/ethyl acetate to give 3.41 g. of crude product. This material was chromatographed over silica gel (180 g.) with 5% methanol in methylene chloride. The first material eluted from the column was crystallized from a methylene chloride/ethyl acetate/-Skellysolve ® B mixture to give 0.37 g., melting point 224°–225.5° of the titled compound (Ib). The analytical sample was recrystallized from a methylene chloride/ethyl acetate and had melting point 224°–225°.

Anal. Calcd. for $C_{16}H_{16}ClN_5$: C, 61.24; H, 5.14; Cl, 11.30; N, 22.32. Found: C, 61.07, H, 5.14; Cl, 11.60; N, 22.34.

The second material eluted from the column was crystallized from methylene chloride/ethyl acetate to give 0.41 g. of 1,2,3,6-tetrahydropyridine hydrochloride, melting point 192.5°–193.5° C. The analytical sample had a melting point 193° C.

Anal. Calcd. for $C_5H_{10}ClN$: C, 50.42; H, 8.39; Cl, 29.51; N, 11.66. Found: C, 49.94; H, 8.52; Cl, 29.79; N, 11.63.

The residues and mixtures of the above two products were combined, mixed with saturated sodium bicarbonate solution and extracted with chloroform. The extract was washed with water, dried (Na₂SO₄) and concentrated. The residue was crystallized from methylene chloride/ethyl acetate to give: 1.0 g., melting point 223.5°-224° C. and 0.32 g., melting point 223.5°-224.5° C. of additional titled compound (Ib).

In the manner given in Example 2, other 1,8-disubstituted-6-(3,6-dihydro-1(2H)-pyridyl)-4H-s-triazolo[4,3-a][1,4]benzodiazepines can be prepared. Representative compounds thus obtained include:
8-Bromo-1-methyl-6-(3,6-dihydro-1(2H)-pyridyl)-4H-s-triazolo[4,3-a][1,4]benzodiazepine,
8-Bromo-1-ethyl-6-(3,6-dihydro-1(2H)-pyridyl)-4H-s-triazolo[4,3-a][1,4]benzodiazepine,
8-Bromo-1-n-propyl-6-(3,6-dihydro-1(2H)-pyridyl)-4H-s-triazolo[4,3-a][1,4]benzodiazepine,
8-Bromo-6-(3,6-dihydro-1(2H)-pyridyl)-4H-s-triazolo[4,3-a][1,4]benzodiazepine,
8-Bromo-1-hydroxymethyl-6-(3,6-dihydro-1(2H)-pyridyl)-4H-s-triazolo[4,3-a][1,4]benzodiazepine,
1-Methyl-6-(3,6-dihydro-1(2H)-pyridyl)-4H-s-triazolo[4,3-a][1,4]benzodiazepine,
1-ethyl-6-(3,6-dihydro-1(2H)-pyridyl-4H-s-triazolo[4,3-a][1,4]benzodiazepine,
1-n-propyl-6-(3,6-dihydro-1(2H)-pyridyl)-4H-s-triazolo[4,3-a][1,4]benzodiazepine,
1-i-propyl-6-(3,6-dihydro-1(2H)-pyridyl)-4H-s-triazolo[4,3-a][1,4]benzodiazepine,
1-(hydroxymethyl)-6-(3,6-dihydro-1(2H)-pyridyl)-4H-s-triazolo[4,3-a][1,4]benzodiazepine,
6-(3,6-dihydro-1(2H)pyridyl)-4H-s-triazolo[4-3-a][1,4]benzodiazepine,
8-Fluoro-1-methyl-6-(3,6-dihydro-1(2H)-pyridyl)-4H-s-triazolo[4,3-a][1,4]benzodiazepine,
8-Fluoro-1-ethyl-6-(3,6-dihydro-1(2H)-pyridyl)-4H-s-triazolo[4,3-a][1,4]benzodiazepine,
8-Fluoro-1-hydroxymethyl-6-(3,6-dihydro-1(2H)-pyridyl)-4H-s-triazolo[4,3-a][1,4]benzodiazepine,
8-Fluoro-6-(3,6-dihydro-1(2H)-pyridyl)-4H-s-triazolo[4,3-a][1,4]benzodiazepine,
8-Chloro-6-(3,6-dihydro-1(2H)-pyridyl)-4H-s-triazolo[4,3-a][1,4]benzodiazepine,
8-Chloro-1-n-propyl-6-(3,6-dihydro-1(2H)-pyridyl)-4H-s-triazolo[4,3-a][1,4]benzodiazepine and the like.

EXAMPLE 3

8-Chloro-1-methyl-6-pyrrolidino-4H-s-triazolo[4,3-a][1,4]benzodiazepine (Ic)

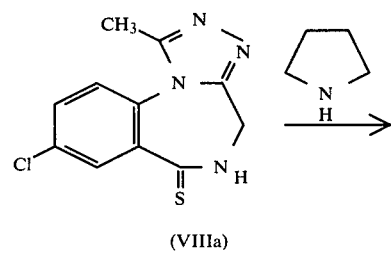

(VIIIa)

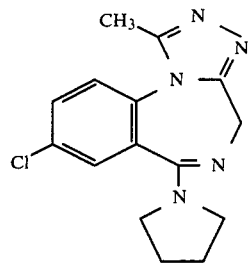

C₁₅H₁₆ClN₅
(Ic)

A stirred mixture of 8-chloro-4,5-dihydro-1-methyl-6H-s-triazolo[4,3-a][1,4]benzodiazepine-6-thione (VIIIa)(2.65 g., 0.01 mole) and pyrrolidine (25 ml.) was refluxed under nitrogen for 10 hours, cooled, mixed with water and extracted with methylene chloride. The extract was washed with water, dried (Na₂SO₄) and concentrated in vacuo. The residue was dissolved in methylene chloride/ethyl acetate, decolorized with charcoal (Darco) and concentrated until the product crystallized. The product was recrystallized from methylene chloride/acetate to give 1.43 g., melting point 223°-225° and 0.10 g., melting point 222°-225° of the titled compound (Ic)(51% yield). The analytical sample had: melting point 223°-225°; uv (EtOH) λ max 210.5 mμ (ε 41,050), 233 (sh 17,700), 287 (sh, 3450), 292 (3550). The ir and nmr spectra support the proposed structure.

Anal Calcd. for C₁₅H₁₆ClN₅: C, 59.70; H, 5.34; Cl, 11.75; N, 23.21. Found: C, 59.61; H, 5.59; Cl, 12.19; N, 23.04.

In the manner given in Example 3, other 1,8-disubstituted-6-pyrrolidino-4H-s-triazolo[4,3-a][1,4]benzodiazepines can be prepared. Representative compounds thus obtained include:
8-Bromo-1-methyl-6-pyrrolidino-4H-s-triazolo[4,3-a][1,4]benzodiazepine,
8-Bromo-1-ethyl-6-pyrrolidino-4H-s-triazolo[4,3-a][1,4]benzodiazepine,
8-Bromo-1-n-propyl-6-pyrrolidino-4H-s-triazolo[4,3-a][1,4]benzodiazepine,
8-Bromo-6-pyrrolidino-4H-s-triazolo[4,3-a][1,4]benzodiazepine,
8-Bromo-1-(hydroxymethyl)-6-pyrrolidino-4H-s-triazolo[4,3-a][1,4]benzodiazepine,
1-Methyl-6-pyrrolidino-4H-s-triazolo[4,3-a][1,4]benzodiazepine,
1-ethyl-6-pyrrolidino-4H-s-triazolo[4,3-a][1,4]benzodiazepine,
1-n-propyl-6-pyrrolidino-4H-s-triazolo[4,3-a][1,4]benzodiazepine,
1-i-propyl-6-pyrrolidino-4H-s-triazolo[4,3-a][1,4]benzodiazepine,
1-(hydroxymethyl)-6-pyrrolidino-4H-s-triazolo[4,3a][1,4]benzodiazepine,
6-pyrrolidino-4H-s-triazolo[4,3-a][1,4]benzodiazepine,
8-Fluoro-1-methyl-6-pyrrolidino-4H-s-triazolo[4,3-a][1,4]benzodiazepine,
8-Fluoro-1-ethyl-6-pyrrolidino-4H-s-triazolo[4,3-a][1,4]benzodiazepine,
8-Fluoro-1-(hydroxymethyl)-6-pyrrolidino-4H-s-triazolo[4,3-a][1,4]benzodiazepine, 8-Fluoro-6-pyrrolidino-4H-s-triazolo[4,3-a][1,4]benzodiazepine,
8-Chloro-6-pyrrolidino-4H-s-triazolo[4,3-a][1,4]benzodiazepine,
8-Chloro-1-n-propyl-6-pyrrolidino-4H-s-triazolo[4,3-a][1,4]benzodiazepine, and the like.

EXAMPLE 4

8-Chloro-1-methyl-4-piperidino-6H-triazolo[4,3-a][1,4]benzodiazepine (Xa);
8-chloro-1-methyl-6-piperidino-4H-s-triazolo[4,3-a][1,4]benzodiazepine (Ia)

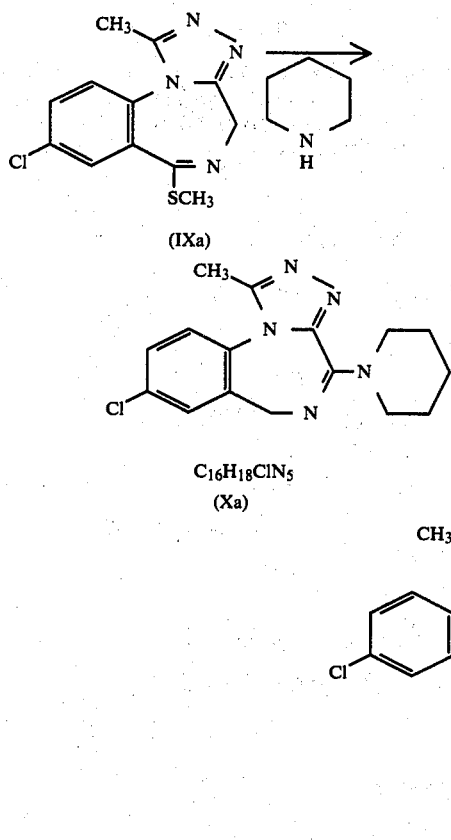

A stirred mixture of 8-chloro-1-methyl-6-(methylthio)-4H-s-triazolo[4,3-a][1,4]benzodiazepine (IXa) (2.79 g., 0.01 mole) and piperidine (20 ml.) was refluxed gently for 48 hours. A slow stream of nitrogen was bubbled through the mixture during this period. The cooled mixture was poured into water and extracted with chloroform. The extract was washed with brine, dried (Na$_2$SO$_4$) and concentrated in vacuo. The residue was chromatographed on silica gel (200 g.) with mixtures of methanol and chloroform containing 3%–5% of methanol. The first product eluted from the column was crystallized from a methanol/ethyl acetate mixture to give: 0.974 g., melting point 204°–206.5° and 0.123 g., melting point 202°–204° of the titled compound (Xa). The analytical sample had melting point 191.5°–192°; however, when the melt was cooled slowly it solidified and then remelted at 203.5°–205.5°.

Anal. Calcd. for C$_{16}$H$_{18}$ClN$_5$: C, 60.85; H, 5.74; Cl, 11.23; N, 22.18. Found: C, 60.67; H, 5.62; Cl, 11.29; N, 22.18.

The second product eluted from the column was crystallized from a methanol/ethyl acetate mixture to give: 0.358 g., melting point 249.5°–251.5° and 0.166 g., melting point 249.5°–251° of the second titled compound (Ia). The ir spectrum of this material was identical to that of Example 1.

EXAMPLE 5

8-Chloro-1-methyl-4-pyrrolidino-6H-s-triazolo[4,3-a][1,4]benzodiazepine (Xb) and
8-chloro-1-methyl-6-pyrrolidino-4H-s-triazolo[4,3-a][1,4]benzodiazepine (Ic)

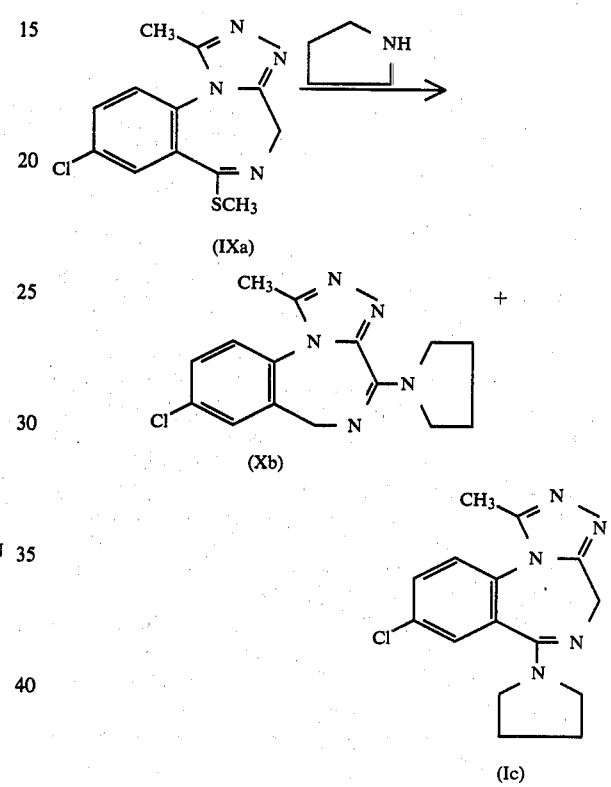

A stirred mixture of 8-chloro-1-methyl-6-(methylthio)-4H-s-triazolo[4,3-a][1,4]benzodiazepine (IXa) (5.58 g., 0.02 mole) and pyrrolidine (30 ml.) was refluxed for 25 hours with a slow stream of nitrogen passing through the mixture; it was kept at ambient temperature for three days and concentrated in vacuo. Xylene, toluene and benzene were used to help remove residual pyrrolidine. The residue was chromatographed on silica gel (250 g.) with 3% methanol in chloroform. The first material eluted from the column was crystallized from a methylene chloride/ethyl acetate/Skellysolve® B mixture to give 1.11 g. of the titled compound (Xb), melting point 216°–217°.

Anal. Calcd. for C$_{15}$H$_{16}$ClN$_5$: C, 59.70; H, 5.34; Cl, 11.75; N, 23.21. Found: C, 59.40; H, 5.37; Cl, 12.19; N, 23.13.

Further elution of the column gave a second product which was crystallized from a methylene chloride/ethyl acetate to give 0.65 g., melting point 222°–223.5° of the titled 6-pyrrolidino compound (Ic).

EXAMPLE 6

8-Chloro-1-methyl-6-morpholino-4H-s-triazolo[4,3-a][1,4]benzodiazepine (Id)

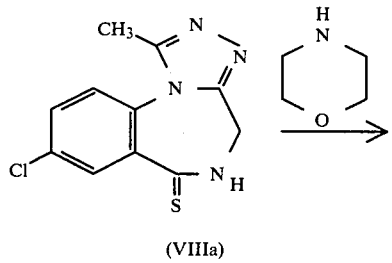

(VIIIa)

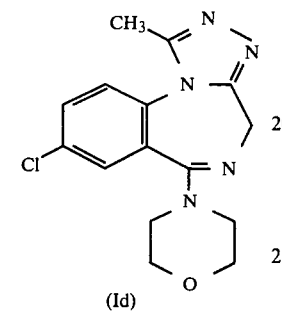

(Id)

A stirred mixture of the 6-thione (VIIIa) (2.65 g., 0.01 mole) and morpholine (25 ml.) was refluxed for 20 hours, under nitrogen, cooled, mixed with cold water and extracted with methylene chloride. The extract was washed with water, then brine, dried ($Na_2SO_4$) and concentrated in vacuo. The solid residue was mixed with ethyl acetate, collected by filtration and recrystallized from a methylene chloride/methanol/ethyl acetate mixture to give 1.21 g., melting point 243°–253° C. of the titled compound (Id)(38% yield). This material had: uv (EtOH) λ max 214 mμ (ε 37,150), 235 (sh, 14,200), 287 (3300), 292 (3300). The ir and nmr spectra support the proposed structure.

Anal. Calcd. for $C_{15}H_{16}ClN_5O$: C, 56.69; H, 5.07; Cl, 11.16; N, 22.04. Found: C, 56.97; H, 5.34; Cl, 11.31; N, 22.10.

In the manner given in Example 6, other 1,8-disubstituted-6-morpholino-4H-s-triazolo[4,3-a][1,4]benzodiazepines can be prepared. Representative compounds thus obtained include:

8-Bromo-1-methyl-6-morpholino-4H-s-triazolo[4,3-a][1,4]benzodiazepine,
8-Bromo-1-ethyl-6-morpholino-4H-s-triazolo[4,3-a][1,4]benzodiazepine,
8-Bromo-1-n-propyl-6-morpholino-4H-s-triazolo[4,3-a][1,4]benzodiazepine,
8-Bromo-6-morpholino-4H-s-triazolo[4,3-a][1,4]benzodiazepine,
8-Bromo-1-(hydroxymethyl)-6-morpholino-4H-s-triazolo[4,3-a][1,4]benzodiazepine,
1-methyl-6-morpholino-4H-s-triazolo[4,3-a][1,4]benzodiazepine,
1-ethyl-6-morpholino-4H-s-triazolo[4,3-a][1,4]benzodiazepine,
1-n-propyl-6-morpholino-4H-s-triazolo[4,3-a][1,4]benzodiazepine,
1-i-propyl-6-morpholino-4H-s-triazolo[4,3-a][1,4]benzodiazepine,
1-(hydroxymethyl)-6-morpholino-4H-s-triazolo[4,3-a][1,4]benzodiazepine,
6-morpholino-4H-s-triazolo[4,3-a][1,4]benzodiazepine,
8-Fluoro-1-methyl-6-morpholino-4H-s-triazolo[4,3-a][1,4]benzodiazepine,
8-Fluoro-1-ethyl-6-morpholino-4H-s-triazolo[1,4]benzodiazepine,
8-Fluoro-1-(hydroxymethyl)-6-morpholino-4H-s-triazolo[4,3-a][1,4]benzodiazepine,
8-Fluoro-6-morpholino-4H-s-triazolo[4,3-a][1,4]benzodiazepine,
8-Chloro-6-morpholino-4H-s-triazolo[4,3-a][1,4]benzodiazepine,
8-Chloro-1-n-propyl-6-morpholino-4H-s-triazolo[4,3-a][1,4]benzodiazepine, and the like,

EXAMPLE 7

8-Chloro-1-methyl-4-morpholino-6H-s-triazolo[4,3-a][1,4]benzodiazepine (Xc);
8-chloro-1-methyl-6-morpholino-4H-s-triazolo[4,3-a][1,4]benzodiazepine (Id)

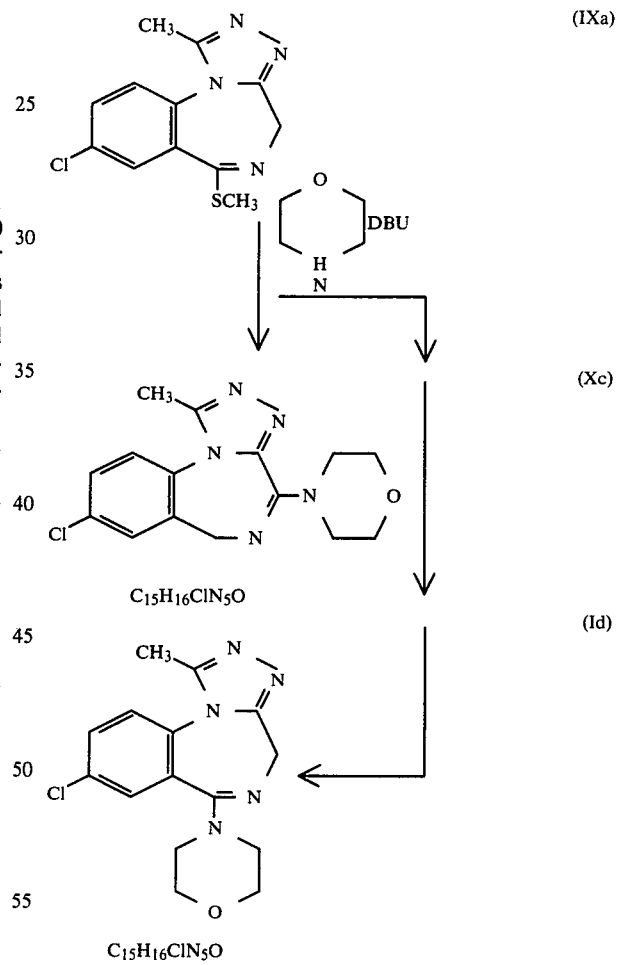

A stirred mixture of the 6-methylthio compound (IXa) (2.79 g., 0.01 mole), morpholine (20 ml.) and 1,5-diazabicyclo[5.4.0]undec-5-ene (DBU, 1.52 g., 0.01 mole) was refluxed for 22 hours with a slow stream of $N_2$ bubbling through the mixture. It was then concentrated in vacuo using xylene and toluene to help remove residual morpholine. The residue was chromatographed on silica gel (160 g.) with 3% $MeOHCHCl_3$. The first material eluted was crystallized from $CH_2Cl_2$-EtOAc-Skelly B to give 1.45 g. of the titled compound (Xc)

melting point 187°–188.5°. The analytical sample was recrystallized from CH₂Cl₂-EtOAc and had melting point 191°–191.5°.

Anal. Calcd. for $C_{15}H_{16}ClN_5O$: C, 59.69; H, 5.08; Cl, 11.16; N, 22.04. Found: C, 56.73; H, 4.99; Cl, 11.24; N, 21.95.

The second product eluted from the column was crystallized from CH₂Cl₂-EtOAc to give 0.73 g. of the titled compound (Id), melting point 257°–258.5°.

EXAMPLE 8

8-Chloro-1-methyl-4-piperidino-6H-s-triazolo[4,3-a][1,4]benzodiazepine (Xa);

8-chloro-1-methyl-6-piperidino-4H-s-triazolo[4,3-a][1,4]benzodiazepine (Ia)

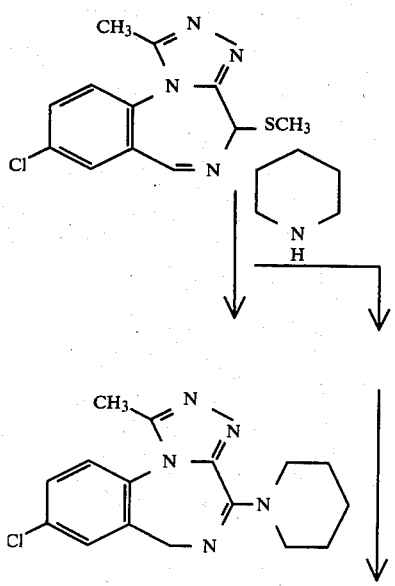

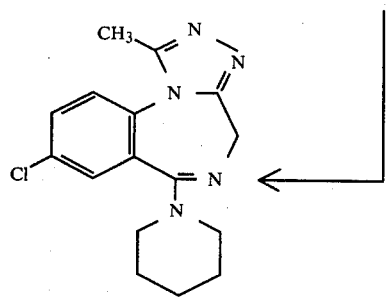

A stirred mixture of the 4-methylthio compound (XIIIa)(0.443 g.) in piperidine (4 ml.) was kept at 115°–117° for 20 hours with a slow stream of N₂ passing through the mixture. It was then mixed with water and extracted with CHCl₃. The extract was washed with brine, dried (NaSO₄) and concentrated. The residue was chromatographed on silica gel (25 g.) with 3% MeOH-CHCl₃. The first product eluted from the column was crystallized from MeOH-EtOAc (Darco) to give 0.051 g., melting point 190.5°–203.5°; 0.042 g., melting point 189°–190°; 0.019 g., melting point 189°–190° and 0.034 g., melting point 189°–190° of the titled compound (Xa).

The second product was crystallized from MeOH—EtOAc (Darco) to give 0.044 g. of the titled compound (Ia), melting point 248°–249°.

I claim:
1. A compound of the formula

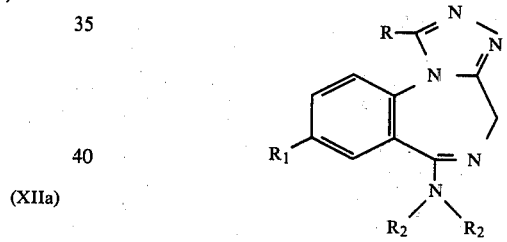

wherein
R is hydrogen, C₁ to C₃-alkyl or hydroxymethyl;
R₁ is hydrogen or a halogen having an atomic number of from 9 to 35; and the two R₂ moieties are taken together with the nitrogen to which they are bonded to complete a 3,6-dihydro-1(2H)-pyridyl nitrogen ring moiety or a pharmacologically acceptable salt thereof.
2. A compound according to claim 1 wherein R is C₁ to C₃-alkyl, R₁ is a halogen having an atomic number of from 9 to 35, and the two R₂ groups are taken together with the nitrogen to which they are bonded to complete a 3,6-dihydro-1(2H)-pyridyl group, and the pharmacologically acceptable salts thereof.
3. A compound according to claim 2 which is 8-chloro-1-methyl-6-(3,6-dihydro-1(2H)-pyridyl)-4H-s-triazolo[4,3-a][1,4]benzodiazepine, and the pharmacologically acceptable salts thereof.

* * * * *